(12) United States Patent
Smith (10) Patent No.: US 8,423,296 B2
(45) Date of Patent: Apr. 16, 2013

(54) METHOD FOR ANALYZING GENE EXPRESSION DATA

(75) Inventor: Yoav Smith, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1012 days.

(21) Appl. No.: 12/083,153

(22) PCT Filed: Oct. 5, 2006

(86) PCT No.: PCT/IL2006/001162
§ 371 (c)(1), (2), (4) Date: Feb. 6, 2009

(87) PCT Pub. No.: WO2007/039906
PCT Pub. Date: Apr. 12, 2007

(65) Prior Publication Data
US 2009/0157324 A1    Jun. 18, 2009

Related U.S. Application Data

(60) Provisional application No. 60/723,916, filed on Oct. 6, 2005.

(51) Int. Cl.
*G06F 7/00* (2006.01)

(52) U.S. Cl.
USPC ................. 702/19; 702/20; 703/11; 707/700; 436/501

(58) Field of Classification Search .................... None
See application file for complete search history.

(56) References Cited

FOREIGN PATENT DOCUMENTS

| WO | 2004/001072 A2 | 12/2003 |
|---|---|---|
| WO | 2004/053074 A2 | 6/2004 |

OTHER PUBLICATIONS

Golub, T. R. et al., "Molecular Classification of Cancer: Class Discovery and Class Prediction by Gene Expression Monitoring", Science, 1999, pp. 531-537, vol. 286.
Mukherjee, S.N. et al., "Gene Ranking Using Bootstrapped P-values," pp. 16-22, vol. 5. Issue No. 2., Department of Engineering Science University of Oxford, Oxford UK. 2003.
Fu, L. M. et al., "Improving Reliability of Gene Selection From Microarray Functional Genomics Data," IEEE Transactions on Information Technology in Biomedicine, 2003, pp. 191-196, vol. 7, No. 3.
Pavlidis, P. et al., "The effect of replication on gene expression microarray experiments", Bioinformatics, 2003, pp. 1620-1627, vol. 19, No. 13, Oxford University Press.
Golub, T. R. et al., "Molecular Classification of Cancer: Class Discovery and Class Prediction by Gene Expression Monitory", Science, 1999, pp. 531-537, vol. 286.
Van't Veer, L. J. et al., "Gene expression profiling predicts clinical outcome of breast cancer," Nature, 2002, pp. 530-536, vol. 415, Macmillan Magazines Ltd.

*Primary Examiner* — Mary Zeman
(74) *Attorney, Agent, or Firm* — Vorys, Sater, Seymour and Pease LLP; Susanne M. Hopkins; Ari G. Zytcer (57) ABSTRACT

The invention provides a method for selecting one or more genes from among a predetermined group of genes whose expression level is significantly different among a first group of individuals in a population in comparison with a second group within the population. The first group of individuals may be, a group of individuals suffering from an illness that responded to a predetermined treatment. The second group of individuals may be a group of individuals suffering from the same illness that did not respond to the treatment. For each of one or more selections of m individuals from the first subset and n individuals from the second subset, the statistical significance of each gene i in the up group of the genes, and in the down group of genes are determined, where the up group is a group of genes for which the expression level in the first group is greater than an expression level in the second group and the down group is a group of genes for which the expression level in the first group is less than an expression level in the second group. The genes in the up and the down groups are ranked according to the number of times each gene received the highest statistical significance among the one or more selections of individuals. A subset of genes in the up group having the highest rankings and a subset of genes in the fown group having the highest rankings are then selected.

8 Claims, 2 Drawing Sheets

FIG. 1

Fig. 2

METHOD FOR ANALYZING GENE EXPRESSION DATA

CROSS-REFERENCE

This is a National Phase Application filed under 35 U.S.C. 371 of International Application No. PCT/IL2006/001162, filed Oct. 5, 2006, claiming the benefit under 35 USC 119(e) of U.S. Provisional Application No. 60/723,916, filed Oct. 6, 2005, the entire content of each of which is hereby incorporated herein by reference in its entirety.

FIELD OF THE INVENTION

This invention relates to methods and systems for analysis of gene expression levels

BACKGROUND OF THE INVENTION

In many medical treatments, such as chemotherapy for cancer patients and Interferon treatment for hepatitis C, administration of the treatment to a group of individuals in the population suffering from an illness can result in inconsistent results in which some of the individuals respond to the treatment while others do not. When the variability in the response has a genetic basis, a genetic analysis, such as microarray technology may be utilized to characterize genetically those individuals that responded to the treatment and those that did not in order to be able to predict which people suffering from the illness would respond to the treatment and which would not.

Figure 1:
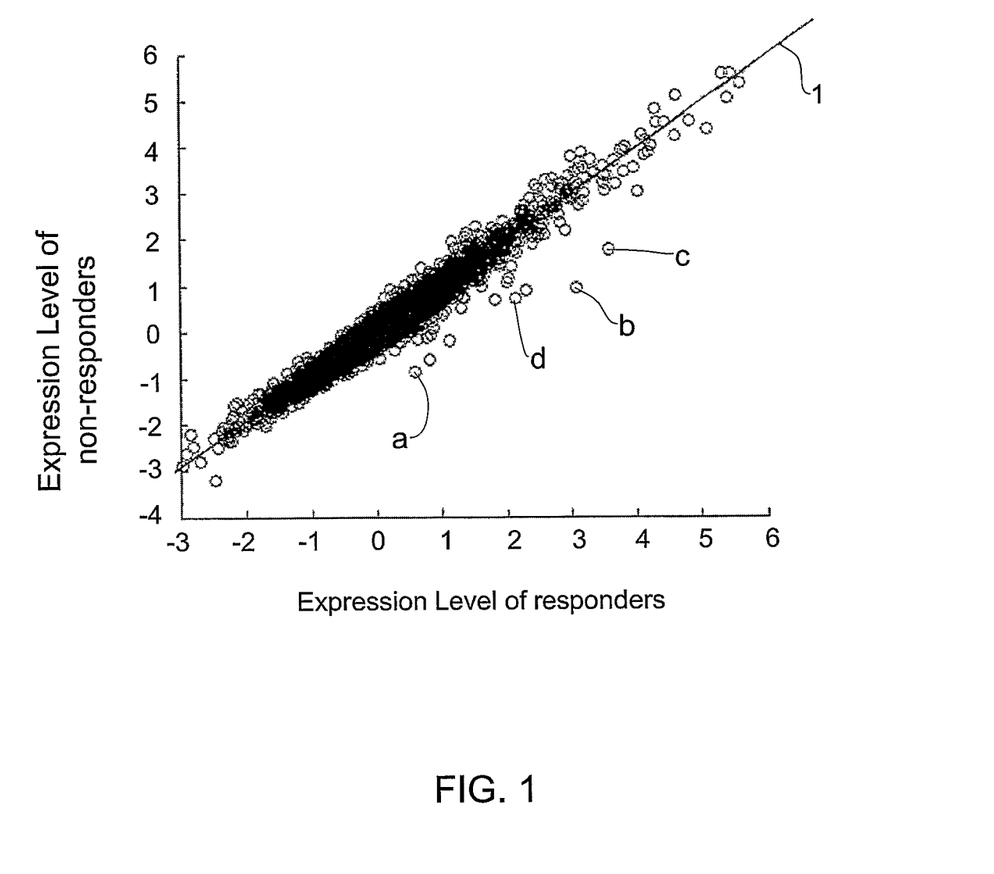
FIG. 1 shows a comparison of the expression level of 15,000 genes in a group of 11 people suffering from hepatitis C that responded to Interferon treatment with that of a group of 11 people suffering from hepatitis C that did not respond to the treatment.

For the vast majority of the genes in the genome, the gene expression level in the individuals that respond to the treatment is not significantly different from those that do not. Only a very small number of genes in the genome show a significant difference in their expression level in the two groups. FIG. 1 compares the expression level of 15,000 genes in a group of 11 people suffering from hepatitis C that responded to Interferon treatment with that of a group of 11 people suffering from hepatitis C that did not respond to the treatment. Each circle in the graph of FIG. 1 represents a different gene and has as its x-coordinate the average expression level of the gene among the 11 people responding to the treatment and as its y-coordinate the average expression level of the gene among the 1 not responding to the treatment. As seen in FIG. 1, the vast majority of the circles are on the line y=x 1, indicating that the expression levels of these genes is essentially the same in both groups. Only a very small proportion of the circles deviate significantly from the line y=x. For example, the genes represented by the circles a, b, c and d have an expression level that is significantly higher in the group responding to the treatment in comparison to the group not responding to the treatment.

DESCRIPTION OF THE INVENTION

In its first aspect, referred to herein as the "learning aspect", the present invention provides a method for selecting one or more genes from among a predetermined group of genes whose expression level is significantly different among a first group of individuals in a population (referred to herein as the "success group") in comparison with a second group within the population (referred to herein as the "failure group"). The success group may be, for example, a group of people suffering from an illness that respond to a particular treatment, and the failure group may be, for example, a group of people suffering from the same illness that do not respond to the treatment. The predetermined group of genes may be, for example, the entire genome, or a predetermined subset of genes in the genome.

The learning aspect of the invention is carried out on a group of individuals referred to as the "learning group". The learning group consists of a first subset of individuals known to belong to the success group, and a second subset of individuals known to belong to the failure group. For each gene i in the predetermined set of genes, the average and the standard deviation of the expression level of the gene in the success subset of the learning group are denoted herein as $\mu_i^s$ and $\sigma_i^s$, respectively. The average and the standard deviation of the expression level of the gene i in the failure subset learning set of the learning group are denoted herein as $\mu_i^f$ and $\sigma_i^f$, respectively. For each individual j, the expression level of the gene i in the individual j is denoted by $a_{ij}$.

In accordance with the learning aspect of the invention, the parameters $\mu_i^s$, $\sigma_i^s$, $\mu_i^f$ and $\sigma_i^f$ are calculated and a statistical test is applied in order to determine for which genes i $\mu_i^s$ and $\mu_i^f$ are significantly different from each other. That is, the genes for which the null hypothesis $\mu_i^f = \mu_i^s$ rejected at a predetermined level of significance. In one preferred embodiment of the invention, a classical t-test is used. The subset of genes in the predetermined set of genes for which $\mu_i^s$ and $\mu_i^f$ are significantly different from each other and for which $\mu_i^f > \mu_i^s$ is called the "down group" of genes, and is denoted herein as the set D. The subset of genes in the predetermined set of genes for which $\mu_i^s$ and $\mu_i^f$ are significantly different from each other and for which $\mu_i^f < \mu_i^s$ is called the "up group" of genes, and is denoted herein as U.

In accordance with the learning aspect of the invention, the following procedure is carried out:

1. For each of one or more selections of an integer m individuals from the success subset of the learning group and an integer n individuals from the failure subset of the learning group, the following procedure is carried out:

(a) The statistical significance of each gene i in the up group of the genes is determined for the selections of individuals. That is, the probability that $\mu_i^s$ and $\mu_i^f$ are different for the gene i.

(b) The statistical significance of each gene i in the down group of the genes is determined for each the selections of individuals.

2. (a) The genes in the up group are ranked according to the number of times each gene received the highest statistical significance among the one or more selections of individuals.

(b) The genes in the down group are ranked according to the number of times each gene received the highest statistical significance among the one or more selections of individuals.

3. (a) A subset of genes in the up group is selected having the highest rankings. This subset of genes is denoted herein as U' and may be determined, for example, as a predetermined number of genes having the highest rankings, or the subset of the genes whose rankings are above a predetermined threshold.

(b) A subset of genes in the down group is selected having the highest rankings. This subset of genes is denoted herein as D' and may be determined, for example, as a predetermined number of genes having the highest rankings, or the subset of the genes whose rankings are above a predetermined threshold.

In a preferred embodiment the following additional steps are carried out.

4. (a) A normalized statistical significance, denoted herein by $a_i$, for each gene i in U', is obtained by the following process:

(i) generating a vector $x^i$, where $\chi_k^i$ is the number of times the gene i received the ranking k among the one or more selections, where k=1 to K, for a predetermined constant K.

(ii) generating a vector y, where $y_k$ is the median statistical significance of the genes in U' having the ranking k among the one or more selections, where k=1 to K.

(ii) normalizing the vector y by dividing $y_k$ by the maximum statistical significance of the genes among the k rankings.

(iii) obtaining $a_i$, a normalized statistical significance for the gene i, as $(x^i \cdot y)/(x^1 \cdot y)$, wherein · indicates the scalar product of two vectors.

(b) A normalized statistical significance, denoted herein by $a_i$, for each gene i in D', is obtained by the following process:

(i) generating a vector $x^i$, where $\chi_k^i$ is the number of times the gene i received the ranking k among the one or more selections, where k=1 to K', for a predetermined constant K.

(ii) generating a vector y, where $y_k$ is the median statistical significance of the genes in D' having the ranking k among the one or more selections, where k=1 to K'.

(ii) normalizing the vector y by dividing $y_k$ by the maximum statistical significance of the genes among the k rankings.

(iii) obtaining $a_i$, a normalized statistical significance for the gene i, as $(x^i \cdot y)/(x^1 \cdot y)$, wherein · indicates the scalar product of two vectors.

In its second aspect, referred to herein as the "testing aspect", the invention provides a method for determining whether an individual j suffering from an illness would respond to a treatment of the illness. In accordance with this aspect of the invention, a test is carried out in order to determine whether an individual j to be tested suffering form the illness would respond to the treatment. The test involves calculating a score, where the score involves the gene expression levels of the individual j, $a_{ij}$, for genes I in U' and D'.

In one embodiment of the testing aspect of the invention, a score $d_j$ of the individual is calculated as $$dj = \sum_{i \in U'} a_i a_{ij} - \sum_{i \in D'} a_i a_{ij},$$

where U', D', $a_i$ and $a_{ij}$, are as defined above. The score $d_j$ is then compared to a cut off value. In a preferred embodiment, the cut-off value is $$\frac{(\mu^s + \sigma^s) + (\mu^f - \sigma^f)}{2},$$

where $\mu^s$, $\sigma^s$, $\mu^f$ and $\sigma^f$ are as defined above. If the score $d_j$ is above the cut off, the individual j is determined to be in the success group, meaning that the individual j would respond to the treatment. If the score dj is below the cut off, the individual j is determined to be in the failure group, meaning that the individual j would not respond to the treatment.

In another embodiment of the invention, a score $d_j$ is calculated as $$dj = \sum_{i \in U'} a_i a_{ij} - \sum_{i \in D'} a_i a_{ij},$$

where U', D', $a_i$ and $a_{ij}$, are as defined above for each individual j in the learning group. The median of the scores $d_j$ in the success group, $m_s$, and the median of the scores in the failure group, $m_f$, of the learning group are calculated. The score dj of the individual to be tested is then calculated, and it is determined to which of the two medians the tested individual's score is closest. If the score is closest to the median of the success group, the individual is determined to belong to the success group, i.e., the individual would respond to the treatment. Otherwise, the individual is determined to belong to the failure group and would not respond to the treatment.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

Thus, in its first aspect, the present invention provides a method for selecting one or more genes from among a predetermined group of genes whose expression level is significantly different among a first group of individuals in a population in comparison with a second group within the population, comprising:

(a) for each of one or more selections of m individuals from the success subset and n individuals from the failure subset:
  (i) determining the statistical significance of each gene i in the up group of the genes, the statistical significance being the probability that $\mu_i^s$ and $\mu_i^f$ are different for the gene i.
  (ii) determining the statistical significance of each gene i in the down group of the genes
(b) ranking the genes in the up group according to the number of times each gene received the highest statistical significance among the one or more selections of individuals;
(c) ranking the genes in the down group according to the number of times each gene received the highest statistical significance among the one or more selections of individuals;
(d) selecting a subset U' of genes in the up group having the highest rankings;
(e) selecting a subset of genes D in the down group having the highest rankings.

In its second aspect, the invention provides a method for determining whether an individual j suffering from an illness would respond to a treatment of the illness comprising
(a) obtaining a normalized statistical significance, $a_i$, for each gene i in U';
(b) obtaining a normalized statistical significance, $a_i$, for each gene i in D',
(c) calculating a score, where the score dj using an algebraic expression involving the gene expression levels of the individual j, $a_{ij}$, for genes i in U' and D'.

In its third aspect, the invention provides a computer program comprising computer program code means performing all the numerical steps of the method of the invention for selecting one or more genes from among a predetermined group of genes whose expression level is significantly different among a first group of individuals in a population in comparison with a second group within the population, when said program is run on a computer.

In its fourth aspect, the invention provides a computer program comprising computer program code means performing all the steps of the method of the invention for selecting one or more genes from among a predetermined group of genes whose expression level is significantly different among a first group of individuals in a population in comparison with a second group within the population embodied on a computer readable medium.

A computer program comprising computer program code means for performing all the numerical steps of the method of the invention for determining whether an individual suffering from an illness would respond to a treatment of the illness when said program is run on a computer.

A computer program comprising computer program code means for performing all the numerical steps of the method of the invention for determining whether an individual suffering from an illness would respond to a treatment of the illness when said program is run on a computer embodied on a computer readable medium.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

EXAMPLES

Example 1

The method of the invention was carried out using data obtained from Van't Veer et al. Nature, vol. 415, Jan. 31, 2002, page 530. The method was carried out on a learning group of 48 individuals suffering from breast cancer. The learning aspect of the invention was carried out on a learning group consisting of 24 individuals that responded to a specific chemotherapy treatment (the success group), and 24 individuals that did not respond to this treatment (the failure group). The method of the invention was carried out in order to select genes whose expression level is significantly different among the success group in comparison to the failure group. A microarray analysis of the gene expression of each of the 100 individuals was obtained. 100 selections of 10 individuals in the success group and 10 individuals in the failure group were made. For each selection the statistical significance of each gene in the genome was determined using the t-test using a significance level of 0.05, and the genes were ranked according to their statistical significance. Tables 1a and 1b show, for each of the 100 selections, the genes having the 10 highest significance in the up group and the down group, respectively. The genes are ranked, with the gene having the highest significance for the election having the ranking 1. Tables 2a and 2b show, for each of the 100 selections, the highest statistical significance obtained in the up group and the down group, respectively. The genes in the up group were then ranked according to the number of selections for which the gene received the highest statistical significance. The genes in the down group were then ranked according to the number of selections for which the gene received the highest statistical significance.

Table 3 shows an analysis of the two genes having the highest ranking among the genes in the up group (genes 22845 and 20252) and the four genes having the highest ranking among the genes in the down group (genes 24143, 4423, 785, and 1236). In the up group, the gene 22845 received the highest ranking 26 times out of 100, and received the second ranking 20 times, and so on, as indicated in Table 3. Similar data are given in Table 3 for the four genes of the down group. The subset U' of the up group was formed by the two genes 22845 and 20252. The group D' was taken as the four genes 24143, 4423, 785, and 1236. Table 3 also shows the values of $a_i$ for the six genes calculated as above.

Figure 2:
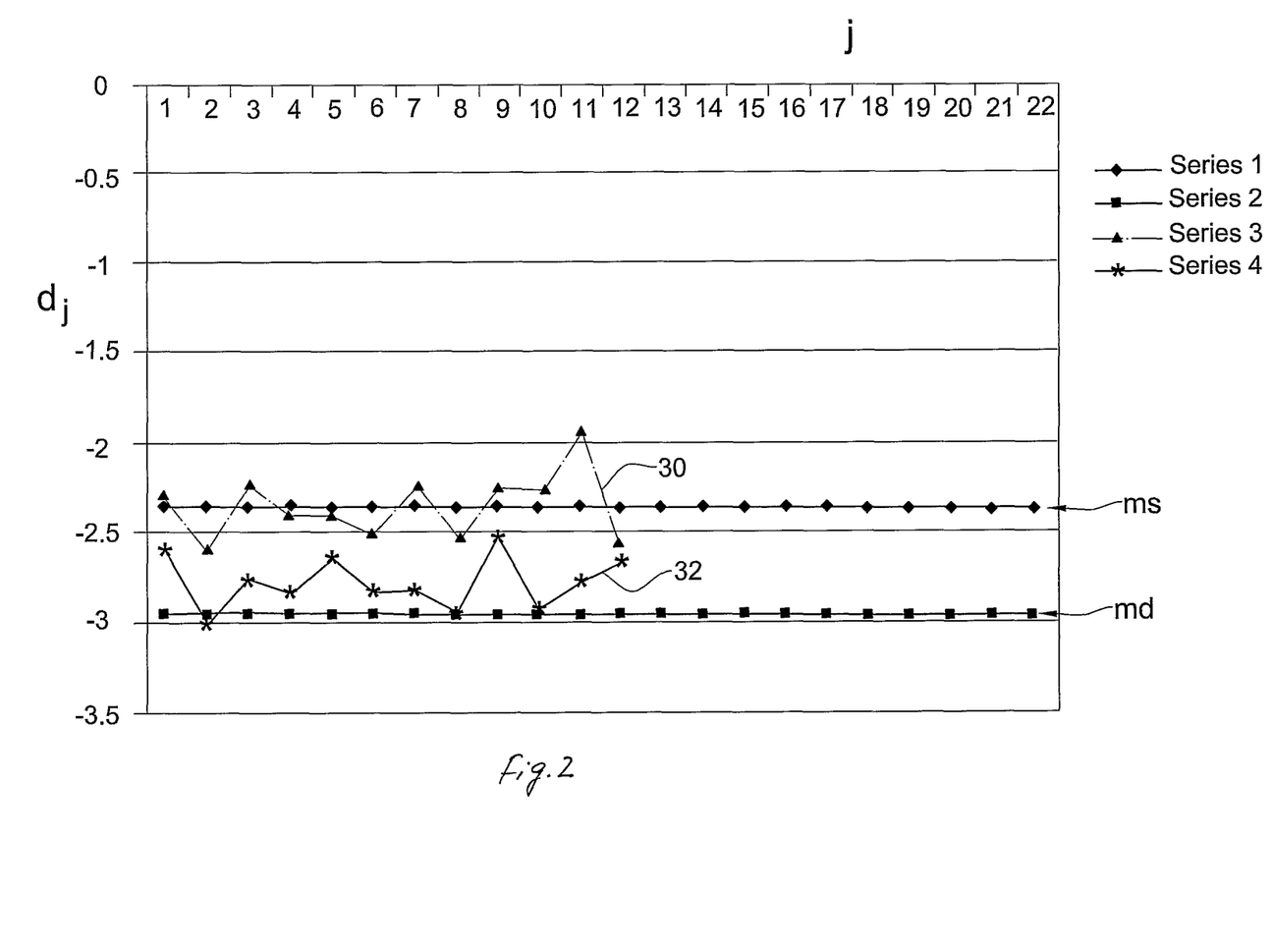
FIG. 2 shows scores of the individuals in a test group that responded to a treatment and scores of the individuals in the test group that did not respond to the treatment.

The testing aspect of the invention was carried out on a testing group consisting of 12 individuals known to have responded to the treatment and another 12 individuals known not to have responded to the treatment. The median score $m_s$ was calculated for a group of 22 individuals in the success subset of the learning group and $m_f$ was calculated for a group of 22 individuals in the failure subset of the learning group. For each individual j, in the test group, the score dj was calculated. In FIG. 2, the scores of the individuals in the test group that responded to the treatment are shown in the curve 30. The scores of the individuals in the test group that did not respond to the treatment are shown in the curve 32. The median $m_s$ and the median $m_f$ are also shown in FIG. 3. All of the data points in the curve 30 are closest to the median $m_s$, showing that the method of the invention correctly identified all 12 of the individuals in the success subset of the testing group. All of the data points in the curve 32 are closest to the median $m_f$, except for the scores of the individuals 1 and 10, showing that the method of the invention correctly identified 10 out of the 12 individuals in the failure subset of the testing group.

Example 2

Hepatitis C virus is a leading cause of chronic liver disease, with over 170 million people infected worldwide. It is also the leading indication for liver transplantation. Complications from chronic hepatitis C infection include cirrhosis, hepatic decompensation, and hepatocellular carcinoma. As a result, treatment strategies to prevent such complications have been widely researched, although many questions remain unanswered. To date, the standard therapy for chronic hepatitis C infection is the combination of peginterferon and .ribavirin. A large proportion of patients do not respond to therapy for reasons that are unclear. The heterogeneity of viral and host phenotypes makes it unlikely that any single factor will accurately predict the cellular response to treatment. The present invention provides a protocol for testing the hypothesis that liver tissue of non-responder and responder are due to differences in gene expression levels and that these differences can be used to predict treatment outcomes which may obviate the need for a therapeutic trial. In accordance with the protocol, patients suffering from chronic HCV infection undergo a liver biopsy prior to treatment and are then treated with a combination of PEGINTERFERON and RIBAVIRIN. The responders and non-responders to this therapy are identified. RNA is extracted from the liver tissue biopsy and the expression of 5 genes (IFI15, IFI616, IFI1, OAS3, OAS2) are checked.

TABLE 1a

| | UP Group | | | | | | | | |
|---|---|---|---|---|---|---|---|---|---|
| | Ranking | | | | | | | | |
| Selection | 1 | 2 | 3 | 4 | 5 | 6 | 7 | 8 | 9 |
| 1 | 14696 | 22845 | 14796 | 8576 | 7947 | 22068 | 11480 | 21585 | 6110 | 15635 |
| 2 | 22845 | 11441 | 10226 | 14696 | 5311 | 19400 | 19467 | 11513 | 7848 | 5900 |
| 3 | 20252 | 22845 | 16894 | 5630 | 10226 | 14981 | 22068 | 3496 | 7265 | 4991 |
| 4 | 9742 | 5423 | 7947 | 2769 | 21773 | 12067 | 10987 | 14705 | 22845 | 8554 |
| 5 | 18425 | 11121 | 10987 | 22845 | 22267 | 16695 | 11145 | 19686 | 6598 | 7797 |
| 6 | 20252 | 22845 | 15548 | 11142 | 17532 | 13425 | 14352 | 14169 | 21585 | 3463 |
| 7 | 6110 | 22845 | 11216 | 14696 | 13621 | 4954 | 10987 | 5900 | 15336 | 9265 |
| 8 | 13189 | 22845 | 16822 | 18048 | 9348 | 14696 | 10987 | 3463 | 21585 | 14169 |
| 9 | 7797 | 13588 | 11441 | 16182 | 14696 | 22845 | 7265 | 15635 | 19840 | 10987 |
| 10 | 22068 | 17878 | 9156 | 17603 | 21585 | 7265 | 18542 | 19467 | 16894 | 22845 |
| 11 | 13588 | 7797 | 15635 | 13621 | 13490 | 14796 | 14705 | 7947 | 8554 |
| 12 | 10226 | 22845 | 9742 | 11441 | 5311 | 7947 | 5630 | 6576 | 7265 | 21585 |
| 13 | 6598 | 14796 | 13588 | 18332 | 20252 | 8067 | 22845 | 8736 | 7265 | 11441 |
| 14 | 13189 | 9730 | 22845 | 7459 | 16822 | 11441 | 21585 | 16894 | 10986 | 23744 |
| 15 | 22845 | 10987 | 13621 | 19400 | 10226 | 5423 | 19686 | 3463 | 5900 | 14696 |
| 16 | 22845 | 6576 | 10226 | 21585 | 19686 | 7265 | 3463 | 17813 | 11142 | 19467 |
| 17 | 22845 | 11480 | 10226 | 6110 | 21585 | 22068 | 9156 | 21329 | 9835 | 19400 |
| 18 | 14796 | 16365 | 22845 | 23774 | 19467 | 10643 | 7797 | 10538 | 16822 | 7459 |
| 19 | 14696 | 13490 | 11441 | 20289 | 8310 | 22845 | 18764 | 9156 | 14352 | 7265 |
| 20 | 16038 | 3463 | 10226 | 22845 | 20252 | 14169 | 13490 | 7848 | 16930 | 9156 |
| 21 | 11441 | 22068 | 7265 | 14352 | 21585 | 4991 | 18109 | 10226 | 4796 | 7910 |
| 22 | 10987 | 13621 | 22845 | 21329 | 19400 | 21585 | 8549 | 5900 | 18425 | 5311 |
| 23 | 22845 | 10987 | 3463 | 13189 | 16038 | 8162 | 21585 | 11441 | 19400 | 5716 |
| 24 | 10987 | 13189 | 22845 | 14342 | 6886 | 19867 | 14696 | 13621 | 10538 | 3463 |
| 25 | 13588 | 22845 | 6541 | 15484 | 17384 | 15336 | 7265 | 6110 | 5900 | 2769 |
| 26 | 20252 | 19840 | 4431 | 7653 | 22845 | 9600 | 13998 | 8179 | 8067 | 7550 |
| 27 | 7265 | 11441 | 6415 | 17603 | 16822 | 15517 | 17345 | 11141 | 19686 | 7848 |
| 28 | 22845 | 14696 | 14324 | 20252 | 15185 | 22068 | 21585 | 4954 | 10987 | 5311 |
| 29 | 13189 | 7459 | 22845 | 23744 | 14324 | 18332 | 21585 | 8554 | 4253 | 19840 |
| 30 | 22845 | 10987 | 7797 | 6110 | 13189 | 14696 | 7947 | 5900 | 21854 | 3463 |
| 31 | 13189 | 22845 | 14696 | 17965 | 18425 | 14324 | 20252 | 21585 | 8576 | −8310 |
| 32 | 10226 | 21585 | 11441 | 22845 | 22068 | 17651 | 13034 | 11480 | 6428 | 13680 |
| 33 | 9156 | 22845 | 10986 | 21585 | 5900 | 10226 | 6110 | 11441 | 22068 | 15407 |
| 34 | 22845 | 11441 | 3463 | 6428 | 9156 | 10036 | 11425 | 5311 | 18561 | 13917 |
| 35 | 22845 | 14796 | 14696 | 10986 | 10987 | 10226 | 20252 | 13490 | 9925 | 14169 |
| 36 | 7797 | 13588 | 11441 | 4253 | 13034 | 8554 | 6598 | 5154 | 19840 | 10987 |
| 37 | 20252 | 11513 | 7797 | 22845 | 11441 | 14696 | 13588 | 10907 | 17785 | 19840 |
| 38 | 9156 | 15407 | 9499 | 22068 | 22845 | 21585 | 11441 | 10226 | 7258 | 11748 |
| 39 | 13588 | 15185 | 7265 | 10327 | 11441 | 12067 | 14705 | 9742 | 16182 | 17353 |
| 40 | 14324 | 9156 | 22845 | 5311 | 7265 | 10226 | 7947 | 14696 | 12348 | 13760 |
| 41 | 22845 | 10226 | 19467 | 16822 | 6576 | 13189 | 10987 | 13621 | 16894 | 14696 |
| 42 | 11441 | 10226 | 17651 | 22845 | 7258 | 20252 | 9601 | 4991 | 22211 | 18109 |
| 43 | 7265 | 21585 | 4991 | 22068 | 8310 | 22845 | 20252 | 10226 | 6110 | 8576 |
| 44 | 7265 | 11121 | 11441 | 16616 | 14754 | 2850 | 21585 | 10226 | 16038 | 15185 |
| 45 | 10987 | 14696 | 18425 | 16695 | 22845 | 13842 | 13621 | 5900 | 18764 | 21585 |
| 46 | 22845 | 9202 | 10226 | 21585 | 10612 | 12528 | 13297 | 22068 | 16822 | 2850 |
| 47 | 22845 | 22068 | 21585 | 11441 | 21587 | 14696 | 3962 | 6110 | 14169 | 5900 |
| 48 | 22845 | 10226 | 22068 | 21585 | 11121 | 9156 | 16616 | 12173 | 9499 | 21854 |
| 49 | 20252 | 22845 | 10987 | 14169 | 10226 | 21304 | 7797 | 10538 | 3463 | 14696 |
| 50 | 20252 | 10226 | 22845 | 18200 | 11513 | 11441 | 19467 | 21585 | 19606 | 22068 |
| 51 | 10226 | 11441 | 15185 | 7265 | 13490 | 20252 | 22845 | 8337 | 18474 | 3496 |
| 52 | 21585 | 18110 | 6110 | 7265 | 5900 | 19467 | 22845 | 22068 | 16798 | 12067 |
| 53 | 13588 | 19467 | 11216 | 4991 | 22186 | 13621 | 14796 | 2769 | 4050 | 15484 |
| 54 | 22845 | 6110 | 14696 | 18474 | 3463 | 10226 | 13189 | 13490 | 15635 | 9156 |
| 55 | 11441 | 18764 | 13189 | 4991 | 16846 | 12067 | 11425 | 17651 | 14432 | 12604 |
| 56 | 10987 | 22845 | 3463 | 4954 | 7126 | 8862 | 13621 | 15635 | 21115 | 23744 |
| 57 | 11441 | 22845 | 9484 | 5900 | 10987 | 21585 | 13621 | 13425 | 8337 |
| 58 | 22845 | 7265 | 13034 | 6110 | 18764 | 11480 | 12067 | 19467 | 15635 | 3463 |
| 59 | 20252 | 19467 | 15635 | 22845 | 16894 | 13917 | 12528 | 10226 | 20390 | 7265 |
| 60 | 22845 | 10226 | 22068 | 6110 | 5311 | 17813 | 6210 | 18425 | 13490 | 7265 |
| 61 | 14696 | 7265 | 19467 | 15484 | 22845 | 2769 | 19840 | 6541 | 11441 |
| 62 | 14696 | 22845 | 9059 | 23030 | 13425 | 19400 | 13621 | 23086 | 14169 | 17802 |
| 63 | 20252 | 4954 | 11441 | 19850 | 9156 | 6110 | 10226 | 4991 | 15336 | 22845 |
| 64 | 7797 | 21585 | 18764 | 12067 | 13588 | 15419 | 10327 | 11441 | 15017 | 3463 |
| 65 | 22845 | 10987 | 8067 | 14696 | 12277 | 12914 | 19840 | 19686 | 9730 |
| 66 | 2850 | 4954 | 11121 | 7265 | 17813 | 6576 | 14352 | 18671 | 21585 | 14754 |
| 67 | 22845 | 11441 | 17570 | 14696 | 10987 | 7910 | 22068 | 10226 | 7797 | 19686 |
| 68 | 14696 | 7797 | 19840 | 15407 | 13842 | 20252 | 22845 | 13588 | 17785 | 5900 |
| 69 | 21585 | 17813 | 22068 | 17603 | 14696 | 6110 | 21652 | 12277 | 19467 | 14324 |
| 70 | 21585 | 7265 | 22068 | 14438 | 18109 | 4991 | 17813 | 11441 | 12067 | 9156 |
| 71 | 22845 | 13621 | 11441 | 14696 | 10987 | 16695 | 19400 | 15874 | 13189 | 15517 |
| 72 | 22845 | 16365 | 2712 | 7797 | 16968 | 14796 | 10987 | 11444 | 14696 | 10538 |
| 73 | 15115 | 14705 | 22845 | 7797 | 19840 | 21585 | 8067 | 7947 | 5423 | 12067 |
| 74 | 3240 | 8554 | 4025 | 22845 | 5962 | 19840 | 5544 | 23744 | 5329 | 9260 |

TABLE 1a-continued

UP Group

| Selection | Ranking | | | | | | | | |
|---|---|---|---|---|---|---|---|---|---|
| | 1 | 2 | 3 | 4 | 5 | 6 | 7 | 8 | 9 |
| 75 | 10987 | 22845 | 13621 | 14796 | 7947 | 10226 | 14169 | 14696 | 19400 | 18764 |
| 76 | 6541 | 6886 | 11121 | 2850 | 5900 | 19840 | 13490 | 11444 | 14754 | 4954 |
| 77 | 22845 | 11441 | 4954 | 7265 | 10226 | 14169 | 5311 | 14796 | 7947 | 21585 |
| 78 | 22845 | 9156 | 10226 | 1831 | 18332 | 7797 | 10643 | 16822 | 19467 | 10987 |
| 79 | 14696 | 19840 | 14796 | 22845 | 10987 | 13588 | 8067 | 6541 | 2769 | 19400 |
| 80 | 20252 | 22845 | 10226 | 20265 | 11317 | 8637 | 16038 | 17661 | 14796 | 9874 |
| 81 | 21585 | 20252 | 19467 | 10226 | 22523 | 4991 | 22068 | 22845 | 7265 | 6110 |
| 82 | 22845 | 14696 | 10226 | 15883 | 14169 | 16038 | 2850 | 13189 | 9156 | 13425 |
| 83 | 16365 | 13621 | 11216 | 14696 | 18671 | 13189 | 14324 | 9742 | 14796 | 12331 |
| 84 | 22068 | 14696 | 10987 | 7910 | 21652 | 22845 | 9172 | 12940 | 15883 | 20252 |
| 85 | 22845 | 10987 | 13621 | 8314 | 14696 | 21585 | 7947 | 18332 | 11513 | 21115 |
| 86 | 20252 | 18148 | 7126 | 22845 | 17424 | 11441 | 4954 | 20453 | 7797 | 17651 |
| 87 | 13621 | 10987 | 14796 | 22845 | 4991 | 11216 | 23086 | 7848 | 7265 | 4954 |
| 88 | 9156 | 10226 | 2850 | 14324 | 4828 | 21585 | 20252 | 5900 | 7265 | 16038 |
| 89 | 10987 | 22845 | 2850 | 6110 | 20252 | 14696 | 22068 | 13034 | 19467 | 10232 |
| 90 | 12277 | 14432 | 13588 | 11441 | 17603 | 14027 | 21652 | 7797 | 17813 | 15982 |
| 91 | 6576 | 21585 | 13189 | 22845 | 7265 | 10226 | 11441 | 12067 | 14796 | 14204 |
| 92 | 7797 | 13185 | 11441 | 13588 | 17651 | 4954 | 12437 | 7848 | 21585 | 12577 |
| 93 | 21585 | 9396 | 22068 | 22845 | 7265 | 1287 | 11441 | 19467 | 9202 | 10226 |
| 94 | 10226 | 22845 | 4796 | 19840 | 11441 | 17039 | 7459 | 9156 | 13842 | 7797 |
| 95 | 22845 | 14696 | 13189 | 16894 | 21585 | 15336 | 7265 | 22068 | 15185 | 5500 |
| 96 | 22845 | 14696 | 15484 | 19467 | 5423 | 5962 | 3463 | 13588 | 11513 | 9600 |
| 97 | 20252 | 22845 | 14696 | 14796 | 10226 | 13621 | 19467 | 11528 | 19400 | 21115 |
| 98 | 19840 | 22845 | 21256 | 20113 | 20480 | 20252 | 19400 | 13998 | 19519 | 9600 |
| 99 | 11441 | 22845 | 13034 | 16695 | 14342 | 21587 | 10226 | 10986 | 15407 | 15298 |
| 100 | 9156 | 11760 | 22845 | 10226 | 14696 | 11441 | 10538 | 21094 | 4954 | 6576 |

TABLE 1b

Down Group

| Selection | Ranking | | | | | | | | | |
|---|---|---|---|---|---|---|---|---|---|---|
| | 1 | 2 | 3 | 4 | 5 | 6 | 7 | 8 | 9 | 10 |
| 1 | 1236 | 578 | 23476 | 24143 | 23004 | 4958 | 1083 | 4423 | 4724 | 23562 |
| 2 | 4423 | 4724 | 785 | 4958 | 8886 | 24143 | 13390 | 18157 | 2540 | 2930 |
| 3 | 4423 | 4958 | 4724 | 23004 | 24143 | 13390 | 578 | 785 | 65 | 1236 |
| 4 | 24143 | 1852 | 1236 | 1083 | 24457 | 578 | 785 | 907 | 150 | 65 |
| 5 | 23965 | 785 | 24143 | 22555 | 4958 | 4423 | 4724 | 578 | 23562 | 21944 |
| 6 | 4423 | 24143 | 2930 | 1663 | 785 | 4724 | 1236 | 23965 | 18157 | 578 |
| 7 | 1236 | 1268 | 578 | 1083 | 24143 | 23476 | 1852 | 4724 | 785 | 22941 |
| 8 | 9646 | 24143 | 23004 | 785 | 4958 | 1236 | 4423 | 13390 | 8886 | 1663 |
| 9 | 1236 | 578 | 24143 | 581 | 4958 | 1852 | 785 | 1268 | 23562 | 1057 |
| 10 | 4423 | 1083 | 23476 | 4724 | 1852 | 1268 | 23562 | 578 | 24143 | 1236 |
| 11 | 785 | 24143 | 1236 | 2540 | 2819 | 4724 | 1268 | 4423 | 578 | 4958 |
| 12 | 4423 | 24143 | 18157 | 785 | 1663 | 2930 | 4724 | 581 | 13390 | 1852 |
| 13 | 785 | 4423 | 1236 | 1751 | 4958 | 65 | 4724 | 24143 | 578 | 15325 |
| 14 | 2540 | 1236 | 65 | 24143 | 785 | 1268 | 13390 | 4724 | 578 | 4958 |
| 15 | 24143 | 727 | 1268 | 1057 | 785 | 13390 | 23562 | 4423 | 578 | 540 |
| 16 | 4423 | 13390 | 4724 | 785 | 1663 | 4958 | 2930 | 1083 | 578 | 18157 |
| 17 | 785 | 5862 | 1083 | 24143 | 578 | 4423 | 13390 | 23965 | 1236 | 696 |
| 18 | 2540 | 785 | 24143 | 4958 | 13390 | 4423 | 18157 | 4724 | 15696 | 8886 |
| 19 | 2540 | 23965 | 13390 | 1663 | 578 | 24143 | 4724 | 1236 | 65 | 5862 |
| 20 | 4958 | 24143 | 5862 | 19238 | 8886 | 4724 | 23004 | 2930 | 23965 | 785 |
| 21 | 24143 | 24296 | 23476 | 1083 | 22389 | 65 | 1852 | 4724 | 18157 | 2540 |
| 22 | 578 | 785 | 24143 | 65 | 1236 | 21944 | 1268 | 3777 | 1026 | 675 |
| 23 | 4423 | 785 | 2540 | 4724 | 19238 | 5862 | 4958 | 18157 | 23965 | 24143 |
| 24 | 1268 | 24143 | 1236 | 785 | 4724 | 4958 | 65 | 19238 | 4423 | 2540 |
| 25 | 1663 | 4958 | 4423 | 13390 | 1236 | 15706 | 1852 | 24143 | 4724 | 1083 |
| 26 | 785 | 4724 | 4423 | 24143 | 23004 | 19238 | 4958 | 2930 | 5223 | 15696 |
| 27 | 24143 | 1083 | 1236 | 578 | 23004 | 1663 | 4423 | 16420 | 23476 | 1268 |
| 28 | 24143 | 65 | 4724 | 785 | 4958 | 1852 | 1236 | 19238 | 4501 | 15325 |
| 29 | 23500 | 17798 | 785 | 24257 | 18157 | 2540 | 24143 | 17016 | 23622 | 4958 |
| 30 | 1236 | 2540 | 578 | 4958 | 13390 | 2755 | 581 | 1663 | 23562 | 1852 |
| 31 | 1083 | 1663 | 1852 | 4958 | 4724 | 578 | 2930 | 4423 | 6625 | 1268 |
| 32 | 4423 | 24143 | 1852 | 1236 | 22941 | 23965 | 4724 | 785 | 2930 | 1663 |
| 33 | 785 | 24143 | 578 | 4724 | 1236 | 4958 | 18157 | 1663 | 24020 | 10889 |
| 34 | 785 | 24143 | 4958 | 2540 | 1236 | 4423 | 4724 | 2930 | 18157 | 20562 |
| 35 | 2540 | 24143 | 785 | 1236 | 1268 | 19238 | 4958 | 4724 | 578 | 23965 |
| 36 | 785 | 24143 | 2540 | 139 | 4958 | 4724 | 4423 | 2930 | 1751 | 1268 |

TABLE 1b-continued

| | \multicolumn{10}{c}{Down Group} |
| | \multicolumn{10}{c}{Ranking} |
| Selection | 1 | 2 | 3 | 4 | 5 | 6 | 7 | 8 | 9 | 10 |
|---|---|---|---|---|---|---|---|---|---|---|
| 37 | 4423 | 24143 | 4958 | 4724 | 785 | 15325 | 49 | 1852 | 1268 | 1236 |
| 38 | 18157 | 785 | 24143 | 13390 | 6209 | 23476 | 17614 | 4423 | 4958 | 20123 |
| 39 | 1852 | 4958 | 13390 | 6209 | 4724 | 4423 | 1268 | 22941 | 578 | 23562 |
| 40 | 4423 | 13390 | 2540 | 23004 | 785 | 4724 | 322 | 21356 | 24143 | 3099 |
| 41 | 4423 | 785 | 4958 | 24143 | 4724 | 1083 | 23004 | 34 | 1236 | 17614 |
| 42 | 1852 | 785 | 24143 | 4724 | 4423 | 65 | 1663 | 4958 | 578 | 1254 |
| 43 | 1663 | 23476 | 6209 | 4724 | 785 | 4423 | 17513 | 23562 | 2930 | 18157 |
| 44 | 1236 | 24143 | 785 | 65 | 1663 | 24020 | 1268 | 4423 | 4288 | 4724 |
| 45 | 20562 | 24143 | 2540 | 2100 | 21944 | 785 | 3777 | 322 | 1268 | 4958 |
| 46 | 24143 | 785 | 4423 | 23004 | 4958 | 13390 | 4724 | 23562 | 1663 | 20123 |
| 47 | 4724 | 1663 | 13390 | 6209 | 4423 | 22389 | 24143 | 1852 | 23476 | 785 |
| 48 | 24143 | 785 | 4423 | 4958 | 18157 | 13390 | 23476 | 4724 | 23562 | 578 |
| 49 | 4423 | 2540 | 1663 | 785 | 13390 | 2930 | 1236 | 4724 | 24143 | 8886 |
| 50 | 24143 | 5862 | 4423 | 4724 | 18157 | 23965 | 578 | 785 | 8886 | 13390 |
| 51 | 24143 | 785 | 4724 | 2930 | 2540 | 1409 | 4958 | 20123 | 1663 | 18157 |
| 52 | 1236 | 13390 | 1663 | 4423 | 785 | 578 | 2540 | 65 | 1852 | 4958 |
| 53 | 1236 | 65 | 1268 | 143 | 578 | 785 | 1524 | 2540 | 1751 | 581 |
| 54 | 2540 | 24143 | 1852 | 23476 | 6209 | 578 | 4958 | 13390 | 785 | 18157 |
| 55 | 785 | 24143 | 2540 | 4423 | 6209 | 4724 | 1083 | 578 | 24020 | 18157 |
| 56 | 785 | 1236 | 4423 | 24143 | 2540 | 1852 | 4724 | 578 | 8886 | 2930 |
| 57 | 24143 | 785 | 4423 | 4724 | 1268 | 1663 | 2540 | 2930 | 65 | 1852 |
| 58 | 24143 | 1268 | 785 | 578 | 1852 | 6209 | 1663 | 1236 | 23476 | 4724 |
| 59 | 4423 | 18157 | 785 | 4958 | 2930 | 24143 | 4724 | 23004 | 24020 | 1663 |
| 60 | 23004 | 10889 | 578 | 1236 | 24143 | 23476 | 8886 | 22389 | 4958 | 20123 |
| 61 | 1236 | 578 | 1852 | 581 | 22941 | 1083 | 2896 | 13390 | 696 | 14671 |
| 62 | 1268 | 24143 | 9646 | 706 | 785 | 1236 | 13390 | 1452 | 578 | 1083 |
| 63 | 1852 | 1663 | 1268 | 1083 | 4724 | 4423 | 24020 | 6209 | 23562 | 16420 |
| 64 | 4423 | 1663 | 1236 | 6209 | 1852 | 13390 | 785 | 2540 | 4958 | 23476 |
| 65 | 2896 | 719 | 1236 | 65 | 2373 | 5153 | 4370 | 5377 | 13390 | 578 |
| 66 | 24143 | 785 | 4724 | 1268 | 578 | 2540 | 4423 | 1236 | 1083 | 6209 |
| 67 | 24143 | 785 | 4724 | 4423 | 4958 | 4062 | 2930 | 134 | 24371 | 24020 |
| 68 | 358 | 19044 | 4958 | 1268 | 6609 | 24143 | 22724 | 1083 | 22389 | 578 |
| 69 | 1236 | 4423 | 24143 | 785 | 4724 | 65 | 1268 | 578 | 1083 | 4958 |
| 70 | 1236 | 65 | 1852 | 1083 | 578 | 23562 | 785 | 1663 | 24143 | 4724 |
| 71 | 1268 | 41 | 2540 | 578 | 65 | 24143 | 1236 | 785 | 1409 | 603 |
| 72 | 24143 | 2540 | 1236 | 1268 | 719 | 1083 | 540 | 22555 | 4958 | 785 |
| 73 | 13390 | 1236 | 581 | 5862 | 22555 | 24143 | 1663 | 23965 | 23562 | 785 |
| 74 | 18157 | 23500 | 24143 | 4958 | 2930 | 1663 | 21194 | 785 | 22389 | 13390 |
| 75 | 719 | 1236 | 24143 | 1268 | 65 | 1852 | 1663 | 578 | 23562 | 581 |
| 76 | 19238 | 24165 | 24143 | 5377 | 13800 | 785 | 21356 | 1236 | 49 | 3224 |
| 77 | 23004 | 23476 | 4423 | 24143 | 13390 | 1236 | 1852 | 581 | 23562 | 22941 |
| 78 | 4423 | 785 | 4958 | 13390 | 4724 | 8886 | 24143 | 18157 | 10889 | 1663 |
| 79 | 4423 | 322 | 1236 | 135 | 1852 | 49 | 24143 | 785 | 1268 |  |
| 80 | 785 | 24143 | 4423 | 2930 | 2540 | 4724 | 4958 | 18157 | 24020 | 10827 |
| 81 | 785 | 4423 | 4724 | 540 | 1236 | 24143 | 1663 | 23004 | 13390 | 1254 |
| 82 | 785 | 24143 | 1663 | 20123 | 2930 | 13390 | 1236 | 24020 | 4724 | 18157 |
| 83 | 1268 | 2761 | 1236 | 24371 | 34 | 785 | 24309 | 65 | 4423 | 24143 |
| 84 | 1268 | 65 | 24143 | 1236 | 2540 | 785 | 4724 | 578 | 1852 | 581 |
| 85 | 785 | 4724 | 24143 | 578 | 4958 | 1236 | 6209 | 2540 | 18157 | 13390 |
| 86 | 4958 | 785 | 4724 | 24143 | 1852 | 1409 | 8886 | 17614 | 4423 | 578 |
| 87 | 396 | 1268 | 2887 | 65 | 15325 | 19238 | 24143 | 785 | 4958 | 1852 |
| 88 | 1236 | 1083 | 4724 | 21356 | 23004 | 1663 | 24143 | 13390 | 4423 | 4958 |
| 89 | 4423 | 785 | 24143 | 4958 | 13390 | 4724 | 1236 | 16420 | 17689 | 578 |
| 90 | 24143 | 785 | 23500 | 578 | 1326 | 1524 | 1268 | 1236 | 4958 | 2930 |
| 91 | 4423 | 13390 | 24143 | 4724 | 1663 | 785 | 1236 | 1268 | 1083 | 6209 |
| 92 | 785 | 4423 | 24020 | 24143 | 1663 | 4958 | 1236 | 578 | 1268 | 4724 |
| 93 | 785 | 24143 | 578 | 23562 | 1663 | 18157 | 22941 | 23476 | 1852 | 4958 |
| 94 | 785 | 24143 | 3492 | 322 | 1026 | 2540 | 23004 | 19473 | 3756 | 10921 |
| 95 | 13390 | 4958 | 4423 | 23562 | 4724 | 1268 | 8886 | 23476 | 1083 | 1852 |
| 96 | 4423 | 13390 | 24143 | 4724 | 1236 | 1663 | 785 | 4958 | 2930 | 16420 |
| 97 | 706 | 24143 | 4423 | 785 | 4724 | 34 | 4958 | 578 | 18157 | 8886 |
| 98 | 785 | 24143 | 4958 | 4724 | 18157 | 4423 | 17614 | 1852 | 10889 | 2930 |
| 99 | 2540 | 24143 | 785 | 2930 | 1852 | 4958 | 4423 | 24020 | 4724 | 1663 |
| 100 | 785 | 1268 | 24143 | 1236 | 13390 | 578 | 1083 | 4724 | 2540 | 4423 |

TABLE 2a

| | Up Group | | | | | | | | | |
|---|---|---|---|---|---|---|---|---|---|---|
| | Ranking | | | | | | | | | |
| Selection | 1 | 2 | 3 | 4 | 5 | 6 | 7 | 8 | 9 | 10 |
| 1 | 6.62E−06 | 6.85E−06 | 2.18E−05 | 3.95E−05 | 4.15E−05 | 4.59E−05 | 5.23E−05 | 6.48E−05 | 8.20E−05 | 8.56E−05 |
| 2 | 1.00E−08 | 1.40E−06 | 1.52E−05 | 2.18E−05 | 3.02E−05 | 3.49E−05 | 3.76E−05 | 3.92E−05 | 4.44E−05 | 8.24E−05 |
| 3 | 4.14E−07 | 4.30E−06 | 2.83E−05 | 5.69E−05 | 8.73E−05 | 0.00017 | 0.000173 | 0.000199 | 0.000226 | 0.000261 |
| 4 | 1.53E−07 | 1.07E−06 | 1.35E−06 | 1.46E−06 | 1.61E−06 | 2.13E−06 | 3.23E−06 | 3.28E−06 | 3.28E−06 | 4.42E−06 |
| 5 | 2.75E−06 | 4.63E−06 | 6.21E−06 | 1.31E−05 | 2.68E−05 | 2.71E−05 | 3.33E−05 | 6.22E−05 | 6.23E−05 | 6.77E−05 |
| 6 | 1.80E−07 | 6.56E−06 | 7.07E−06 | 1.21E−05 | 1.38E−05 | 1.68E−05 | 1.83E−05 | 1.92E−05 | 2.67E−05 | 2.74E−05 |
| 7 | 6.27E−07 | 1.33E−06 | 1.77E−06 | 3.74E−06 | 4.17E−06 | 7.31E−06 | 8.18E−06 | 8.78E−06 | 1.09E−05 | 2.03E−05 |
| 8 | 6.59E−07 | 2.04E−06 | 4.43E−06 | 7.98E−06 | 1.56E−05 | 1.57E−05 | 1.67E−05 | 1.93E−05 | 2.15E−05 | 2.82E−05 |
| 9 | 5.50E−07 | 2.31E−06 | 3.30E−06 | 3.60E−06 | 6.70E−06 | 9.70E−06 | 1.21E−05 | 1.22E−05 | 2.43E−05 | 3.03E−05 |
| 10 | 6.13E−07 | 1.04E−05 | 1.67E−06 | 2.06E−05 | 2.39E−05 | 3.37E−05 | 3.62E−05 | 3.63E−05 | 3.94E−05 | 4.54E−05 |
| 11 | 2.38E−08 | 5.08E−07 | 1.56E−06 | 2.45E−06 | 3.58E−06 | 4.41E−06 | 4.50E−06 | 4.58E−06 | 5.19E−06 | 6.06E−06 |
| 12 | 1.06E−06 | 1.43E−06 | 4.08E−06 | 1.52E−05 | 2.78E−05 | 3.02E−05 | 3.18E−05 | 4.03E−05 | 4.31E−05 | 4.61E−05 |
| 13 | 1.84E−06 | 4.64E−06 | 2.24E−05 | 4.99E−05 | 5.02E−05 | 5.02E−05 | 5.37E−05 | 5.54E−05 | 5.70E−05 | 6.27E−05 |
| 14 | 2.50E−06 | 5.37E−06 | 2.25E−05 | 2.83E−05 | 6.30E−05 | 7.00E−05 | 7.08E−05 | 9.24E−05 | 9.39E−05 | 9.68E−05 |
| 15 | 1.18E−09 | 8.66E−08 | 2.13E−07 | 4.15E−07 | 9.48E−07 | 2.37E−06 | 3.03E−06 | 5.17E−06 | 6.49E−06 | 6.88E−06 |
| 16 | 2.16E−07 | 4.02E−07 | 1.49E−06 | 2.81E−06 | 5.86E−06 | 1.19E−05 | 1.43E−05 | 1.63E−05 | 2.06E−05 | 2.68E−05 |
| 17 | 7.78E−07 | 1.23E−05 | 2.66E−05 | 4.00E−05 | 6.01E−05 | 6.69E−05 | 7.02E−05 | 9.76E−05 | 0.000118 | 0.000124 |
| 18 | 1.71E−05 | 2.26E−05 | 2.29E−05 | 3.12E−05 | 3.97E−05 | 4.70E−05 | 4.90E−05 | 4.99E−05 | 5.55E−05 | 5.68E−05 |
| 19 | 2.46E−07 | 8.22E−07 | 3.22E−06 | 6.05E−06 | 7.04E−06 | 7.20E−06 | 7.22E−06 | 8.39E−06 | 8.69E−06 | 9.59E−06 |
| 20 | 2.02E−06 | 6.61E−06 | 7.54E−06 | 1.18E−05 | 1.82E−05 | 2.50E−05 | 2.55E−05 | 2.91E−05 | 5.41E−05 | 5.89E−05 |
| 21 | 3.82E−06 | 6.15E−06 | 7.89E−06 | 1.14E−05 | 2.01E−05 | 2.20E−05 | 2.42E−05 | 2.72E−05 | 3.81E−05 | 5.85E−05 |
| 22 | 1.94E−08 | 5.04E−08 | 1.61E−07 | 4.51E−07 | 2.11E−06 | 6.26E−06 | 6.49E−06 | 6.51E−06 | 7.88E−06 | 8.91E−06 |
| 23 | 4.45E−07 | 3.84E−06 | 8.22E−06 | 1.84E−05 | 2.61E−05 | 2.98E−05 | 3.96E−05 | 6.53E−05 | 6.84E−05 | 7.45E−05 |
| 24 | 9.91E−07 | 8.93E−06 | 1.24E−05 | 1.42E−05 | 1.50E−05 | 1.70E−05 | 1.73E−05 | 1.82E−05 | 1.88E−05 | 2.06E−05 |
| 25 | 6.32E−06 | 7.29E−06 | 7.65E−06 | 8.53E−06 | 8.90E−06 | 9.26E−06 | 9.86E−06 | 1.04E−05 | 1.26E−05 | 1.71E−05 |
| 26 | 6.40E−07 | 1.92E−06 | 9.76E−06 | 9.95E−06 | 1.00E−05 | 1.02E−05 | 1.15E−05 | 1.65E−05 | 2.39E−05 | 4.26E−05 |
| 27 | 2.24E−06 | 3.76E−06 | 4.06E−06 | 1.04E−05 | 1.28E−05 | 1.43E−05 | 1.68E−05 | 2.01E−05 | 2.16E−05 | 2.26E−05 |
| 28 | 2.28E−05 | 3.26E−05 | 3.32E−05 | 3.71E−05 | 5.11E−05 | 5.80E−05 | 8.60E−05 | 0.000148 | 0.000149 | 0.00026 |
| 29 | 1.62E−05 | 3.82E−05 | 6.27E−05 | 6.97E−05 | 7.15E−05 | 7.69E−05 | 7.98E−05 | 8.85E−05 | 0.000111 | 0.00016 |
| 30 | 4.61E−07 | 4.68E−06 | 6.45E−06 | 8.12E−06 | 1.13E−05 | 2.28E−05 | 2.37E−05 | 2.75E−05 | 3.01E−05 | 3.38E−05 |
| 31 | 7.74E−08 | 4.80E−07 | 8.69E−06 | 1.17E−05 | 1.30E−05 | 1.51E−05 | 1.69E−05 | 2.08E−05 | 2.48E−05 | 2.59E−05 |
| 32 | 2.03E−05 | 3.27E−05 | 3.42E−05 | 3.66E−05 | 7.60E−05 | 0.000163 | 0.000166 | 0.000167 | 0.000247 | 0.000249 |
| 33 | 4.43E−06 | 6.13E−06 | 1.52E−05 | 1.56E−05 | 2.50E−05 | 2.72E−05 | 4.00E−05 | 4.62E−05 | 5.36E−05 | 8.04E−05 |
| 34 | 5.13E−06 | 6.82E−06 | 9.39E−06 | 1.01E−05 | 1.28E−05 | 1.71E−05 | 1.74E−05 | 2.18E−05 | 3.07E−05 | 3.08E−05 |
| 35 | 5.03E−07 | 1.06E−05 | 3.32E−05 | 3.63E−05 | 4.29E−05 | 4.36E−05 | 5.99E−05 | 7.24E−05 | 8.06E−05 | 8.69E−05 |
| 36 | 2.82E−06 | 3.27E−06 | 3.43E−06 | 7.26E−06 | 9.71E−06 | 9.83E−06 | 1.11E−05 | 1.59E−05 | 1.76E−05 | 1.79E−05 |
| 37 | 1.56E−08 | 1.30E−07 | 3.13E−07 | 5.66E−07 | 1.63E−06 | 2.08E−06 | 6.05E−06 | 6.47E−06 | 7.11E−06 | 8.00E−06 |
| 38 | 9.20E−07 | 1.53E−06 | 1.59E−06 | 3.30E−06 | 5.43E−06 | 6.79E−06 | 1.36E−05 | 2.83E−05 | 7.45E−05 | 8.12E−05 |
| 39 | 4.55E−06 | 4.60E−06 | 6.77E−06 | 7.55E−06 | 9.34E−06 | 1.11E−05 | 1.21E−05 | 1.29E−05 | 2.10E−05 | 2.16E−05 |
| 40 | 2.64E−07 | 4.21E−07 | 1.28E−06 | 1.90E−06 | 2.87E−06 | 2.94E−06 | 5.23E−06 | 5.47E−06 | 5.54E−06 | 6.59E−06 |
| 41 | 3.92E−07 | 8.62E−07 | 1.61E−06 | 2.69E−06 | 1.06E−05 | 1.14E−05 | 1.24E−05 | 1.51E−05 | 1.67E−05 | 2.71E−05 |
| 42 | 2.71E−06 | 9.92E−06 | 1.86E−05 | 2.47E−05 | 6.57E−05 | 6.91E−05 | 7.73E−05 | 0.000121 | 0.000164 | 0.000196 |
| 43 | 3.75E−08 | 4.97E−07 | 8.22E−07 | 1.11E−06 | 1.47E−06 | 1.87E−06 | 3.68E−06 | 4.72E−06 | 8.87E−06 | 9.80E−06 |
| 44 | 4.15E−05 | 4.82E−05 | 5.55E−05 | 6.14E−05 | 6.42E−05 | 6.71E−05 | 7.23E−05 | 7.69E−05 | 7.92E−05 | 7.98E−05 |
| 45 | 2.02E−07 | 1.40E−06 | 2.32E−06 | 3.42E−06 | 4.10E−06 | 1.23E−05 | 1.27E−05 | 1.62E−05 | 1.81E−05 | 1.98E−05 |
| 46 | 4.29E−06 | 8.21E−06 | 1.05E−05 | 1.81E−05 | 6.41E−05 | 6.67E−05 | 8.11E−05 | 9.01E−05 | 0.000103 | 0.000104 |
| 47 | 4.29E−06 | 4.89E−06 | 6.13E−06 | 6.30E−06 | 7.01E−06 | 1.04E−05 | 3.28E−05 | 4.25E−05 | 4.75E−05 | 6.06E−05 |
| 48 | 3.54E−06 | 9.11E−06 | 1.17E−05 | 1.18E−05 | 1.39E−05 | 1.82E−05 | 3.28E−05 | 4.28E−05 | 4.30E−05 | 4.65E−05 |
| 49 | 2.85E−07 | 5.92E−07 | 1.23E−06 | 1.47E−06 | 4.80E−06 | 5.19E−06 | 6.35E−06 | 1.00E−05 | 1.24E−05 | 1.31E−05 |
| 50 | 6.85E−08 | 1.35E−07 | 1.10E−06 | 1.73E−06 | 3.26E−05 | 3.31E−05 | 3.42E−05 | 3.66E−05 | 4.52E−05 | 4.79E−05 |
| 51 | 2.60E−06 | 2.37E−05 | 3.04E−05 | 3.61E−05 | 3.74E−05 | 3.93E−05 | 4.25E−05 | 7.30E−05 | 7.94E−05 | 0.000109 |
| 52 | 2.06E−06 | 4.94E−07 | 1.49E−06 | 1.85E−06 | 1.90E−06 | 6.61E−06 | 8.51E−06 | 8.89E−06 | 1.01E−05 | 1.09E−05 |
| 53 | 2.53E−07 | 3.52E−07 | 3.91E−07 | 6.57E−07 | 8.48E−07 | 3.68E−06 | 4.22E−06 | 4.67E−06 | 5.01E−06 | 9.13E−06 |
| 54 | 1.12E−06 | 1.12E−05 | 1.19E−05 | 1.24E−05 | 1.34E−05 | 1.47E−05 | 2.44E−05 | 2.96E−05 | 3.24E−05 | 3.53E−05 |
| 55 | 1.23E−08 | 1.52E−06 | 2.07E−06 | 2.63E−06 | 2.65E−06 | 2.68E−06 | 3.37E−06 | 4.01E−06 | 1.07E−05 | 1.14E−05 |
| 56 | 8.35E−07 | 9.78E−07 | 5.51E−06 | 1.28E−05 | 3.00E−05 | 3.44E−05 | 3.83E−05 | 6.73E−05 | 8.00E−05 | 8.95E−05 |
| 57 | 5.94E−06 | 1.05E−05 | 2.20E−05 | 3.68E−05 | 3.90E−05 | 4.16E−05 | 4.99E−05 | 6.69E−05 | 7.43E−05 | 8.46E−05 |
| 58 | 2.74E−06 | 3.37E−06 | 4.32E−06 | 5.04E−06 | 5.79E−06 | 7.79E−06 | 7.79E−06 | 8.09E−06 | 8.28E−06 | 8.37E−06 |
| 59 | 2.77E−06 | 1.09E−05 | 1.37E−05 | 2.29E−05 | 3.37E−05 | 3.93E−05 | 5.45E−05 | 6.88E−05 | 8.31E−05 | 9.13E−05 |
| 60 | 1.35E−06 | 3.16E−06 | 3.92E−06 | 1.57E−05 | 1.59E−05 | 2.07E−05 | 3.01E−05 | 3.55E−05 | 4.05E−05 | 4.13E−05 |
| 61 | 7.13E−06 | 9.01E−06 | 1.19E−05 | 1.75E−05 | 1.99E−05 | 2.26E−05 | 2.41E−05 | 4.61E−05 | 5.97E−05 | 6.08E−05 |
| 62 | 1.65E−08 | 2.51E−08 | 9.00E−07 | 1.37E−06 | 3.08E−06 | 4.24E−06 | 6.78E−06 | 7.29E−06 | 1.05E−05 | 1.07E−05 |
| 63 | 2.60E−07 | 4.26E−07 | 6.14E−07 | 1.35E−06 | 2.06E−06 | 2.14E−06 | 3.45E−06 | 3.75E−06 | 8.52E−06 | 1.56E−05 |
| 64 | 2.13E−06 | 5.63E−06 | 5.70E−06 | 5.77E−06 | 6.10E−06 | 1.21E−05 | 2.11E−05 | 2.85E−05 | 3.13E−05 | 3.31E−05 |
| 65 | 7.92E−08 | 6.80E−07 | 9.76E−07 | 1.56E−06 | 1.80E−06 | 1.92E−06 | 2.12E−06 | 3.60E−06 | 3.71E−06 | 5.69E−06 |
| 66 | 2.06E−06 | 2.32E−06 | 6.30E−06 | 1.06E−05 | 2.07E−05 | 2.34E−05 | 2.80E−05 | 3.24E−05 | 3.39E−05 | 3.80E−05 |
| 67 | 7.12E−07 | 3.93E−06 | 1.17E−05 | 1.39E−05 | 1.69E−05 | 1.92E−05 | 2.25E−05 | 2.50E−05 | 2.55E−05 | 3.53E−05 |
| 68 | 5.71E−07 | 2.03E−06 | 2.29E−06 | 3.43E−06 | 4.36E−06 | 5.44E−06 | 8.93E−06 | 9.43E−06 | 1.01E−05 | 1.24E−05 |
| 69 | 4.04E−06 | 4.26E−06 | 5.74E−06 | 8.73E−06 | 9.00E−06 | 9.40E−06 | 1.56E−05 | 1.69E−05 | 2.12E−05 | 2.21E−05 |
| 70 | 1.35E−06 | 3.54E−06 | 5.09E−06 | 5.49E−06 | 8.54E−06 | 1.05E−05 | 1.09E−05 | 1.17E−05 | 1.71E−05 | 1.85E−05 |
| 71 | 4.11E−08 | 2.70E−07 | 1.21E−06 | 1.55E−06 | 3.21E−06 | 5.01E−06 | 5.11E−06 | 5.39E−06 | 5.62E−06 | 1.05E−05 |
| 72 | 3.62E−06 | 7.04E−06 | 1.74E−05 | 1.87E−05 | 2.03E−05 | 3.63E−05 | 4.02E−05 | 4.05E−05 | 4.94E−05 | 5.81E−05 |
| 73 | 6.41E−07 | 8.89E−07 | 1.24E−06 | 1.43E−06 | 3.20E−06 | 3.21E−06 | 3.27E−06 | 3.76E−06 | 5.10E−06 | 6.23E−06 |
| 74 | 1.03E−06 | 1.40E−06 | 1.93E−06 | 2.06E−06 | 4.16E−06 | 4.25E−06 | 4.32E−06 | 5.79E−06 | 8.72E−06 | 1.02E−05 |

TABLE 2a-continued

Up Group

| Selection | Ranking | | | | | | | | | |
|---|---|---|---|---|---|---|---|---|---|---|
| | 1 | 2 | 3 | 4 | 5 | 6 | 7 | 8 | 9 | 10 |
| 75 | 3.20E−07 | 1.09E−06 | 2.65E−06 | 6.13E−06 | 1.54E−05 | 1.80E−05 | 3.84E−05 | 5.14E−05 | 5.39E−05 | 5.85E−05 |
| 76 | 4.06E−06 | 4.39E−06 | 6.45E−06 | 7.07E−06 | 1.40E−05 | 1.50E−05 | 1.60E−05 | 1.82E−05 | 1.89E−05 | 1.99E−05 |
| 77 | 3.13E−06 | 9.80E−06 | 1.07E−05 | 1.09E−05 | 3.37E−05 | 3.49E−05 | 3.61E−05 | 3.71E−05 | 4.43E−05 | 5.69E−05 |
| 78 | 3.99E−06 | 5.07E−06 | 6.74E−06 | 1.62E−05 | 1.85E−05 | 1.96E−05 | 2.07E−05 | 2.40E−05 | 2.95E−05 | 3.30E−05 |
| 79 | 9.74E−07 | 4.10E−06 | 4.58E−06 | 8.02E−06 | 9.60E−06 | 1.08E−05 | 1.53E−05 | 1.74E−05 | 1.81E−05 | 1.90E−05 |
| 80 | 4.73E−06 | 1.18E−05 | 3.00E−05 | 3.57E−05 | 4.55E−05 | 4.96E−05 | 6.22E−05 | 6.82E−05 | 7.78E−05 | 8.09E−05 |
| 81 | 4.49E−06 | 5.14E−06 | 5.21E−06 | 7.58E−06 | 9.95E−06 | 1.07E−05 | 1.56E−05 | 3.33E−05 | 3.61E−05 | 3.82E−05 |
| 82 | 1.42E−07 | 1.78E−06 | 1.05E−05 | 1.50E−05 | 1.74E−05 | 1.93E−05 | 2.21E−05 | 3.04E−05 | 3.09E−05 | 3.42E−05 |
| 83 | 2.99E−07 | 6.73E−07 | 1.96E−06 | 3.63E−06 | 4.31E−06 | 5.34E−06 | 6.30E−06 | 7.94E−06 | 9.16E−06 | 1.03E−05 |
| 84 | 1.57E−06 | 4.08E−06 | 1.19E−05 | 1.22E−05 | 1.46E−05 | 1.60E−05 | 1.64E−05 | 2.06E−05 | 2.09E−05 | 2.65E−05 |
| 85 | 2.88E−08 | 1.74E−06 | 3.82E−06 | 9.56E−06 | 1.09E−05 | 1.40E−05 | 1.59E−05 | 1.96E−05 | 2.34E−05 | 2.34E−05 |
| 86 | 4.39E−06 | 2.80E−05 | 6.91E−05 | 7.07E−05 | 7.97E−05 | 8.67E−05 | 9.05E−05 | 0.000108 | 0.000119 | 0.000134 |
| 87 | 1.93E−06 | 2.39E−06 | 4.95E−06 | 8.42E−06 | 2.82E−05 | 2.84E−05 | 3.76E−05 | 3.93E−05 | 4.60E−05 | 5.22E−05 |
| 88 | 7.22E−07 | 1.23E−06 | 2.58E−06 | 1.27E−05 | 1.97E−05 | 2.06E−05 | 2.08E−05 | 2.28E−05 | 3.40E−05 | 3.51E−05 |
| 89 | 1.56E−05 | 3.79E−05 | 4.32E−05 | 5.95E−05 | 7.36E−05 | 8.36E−05 | 9.73E−05 | 0.00017 | 0.00018 | 0.0002 |
| 90 | 3.46E−06 | 4.61E−06 | 7.08E−06 | 7.27E−06 | 1.18E−05 | 2.03E−05 | 2.04E−05 | 2.65E−05 | 2.72E−05 | 3.72E−05 |
| 91 | 9.26E−07 | 2.69E−06 | 3.49E−06 | 5.61E−06 | 6.58E−06 | 8.07E−06 | 8.70E−06 | 1.25E−05 | 1.29E−05 | 1.60E−05 |
| 92 | 5.28E−07 | 8.89E−07 | 1.08E−06 | 1.13E−06 | 1.45E−06 | 1.75E−06 | 2.58E−06 | 3.73E−06 | 4.48E−06 | 5.46E−06 |
| 93 | 4.84E−06 | 1.85E−05 | 2.92E−05 | 3.38E−05 | 3.78E−05 | 4.37E−05 | 5.81E−05 | 0.000126 | 0.000128 | 0.000134 |
| 94 | 6.90E−06 | 1.58E−05 | 2.84E−05 | 3.30E−05 | 3.33E−05 | 3.39E−05 | 3.96E−05 | 4.03E−05 | 4.57E−05 | 4.86E−05 |
| 95 | 3.12E−07 | 8.80E−07 | 1.21E−06 | 4.63E−06 | 1.06E−05 | 1.42E−05 | 1.74E−05 | 2.29E−05 | 2.36E−05 | 2.56E−05 |
| 96 | 3.27E−06 | 9.90E−06 | 1.32E−05 | 1.53E−05 | 1.86E−05 | 1.94E−05 | 2.36E−05 | 3.06E−05 | 3.30E−05 | 3.64E−05 |
| 97 | 1.05E−09 | 5.81E−07 | 1.59E−06 | 4.39E−06 | 4.50E−06 | 7.86E−06 | 1.20E−05 | 1.40E−05 | 2.52E−05 | 2.98E−05 |
| 98 | 4.87E−07 | 1.05E−06 | 3.34E−06 | 3.55E−06 | 6.26E−06 | 6.48E−06 | 7.35E−06 | 9.38E−06 | 1.38E−05 | 1.54E−05 |
| 99 | 5.01E−06 | 2.21E−05 | 2.34E−05 | 2.92E−05 | 3.83E−05 | 4.87E−05 | 6.53E−05 | 7.50E−05 | 8.20E−05 | 8.59E−05 |
| 100 | 6.62E−07 | 4.56E−06 | 6.37E−06 | 1.74E−05 | 2.81E−05 | 2.87E−05 | 4.12E−05 | 4.24E−05 | 6.47E−05 | 6.55E−05 |

TABLE 2b

Down Group

| Selection | Ranking | | | | | | | | | |
|---|---|---|---|---|---|---|---|---|---|---|
| | 1 | 2 | 3 | 4 | 5 | 6 | 7 | 8 | 9 | 10 |
| 1 | 1.04E−06 | 2.80E−06 | 4.81E−06 | 6.63E−06 | 6.67E−06 | 7.36E−06 | 8.30E−06 | 8.90E−06 | 9.45E−06 | 1.16E−05 |
| 2 | 1.15E−07 | 6.87E−07 | 2.52E−06 | 3.04E−06 | 7.76E−06 | 8.85E−06 | 9.90E−06 | 1.04E−05 | 1.44E−05 | 1.83E−05 |
| 3 | 6.40E−06 | 6.72E−06 | 1.23E−05 | 1.45E−05 | 1.76E−05 | 3.31E−05 | 3.65E−05 | 4.41E−05 | 5.23E−05 | 5.54E−05 |
| 4 | 3.30E−07 | 3.56E−07 | 1.10E−06 | 1.86E−06 | 1.86E−06 | 2.42E−06 | 5.18E−06 | 5.75E−06 | 7.57E−06 | 7.75E−06 |
| 5 | 2.73E−05 | 3.40E−05 | 4.80E−05 | 4.99E−05 | 7.14E−05 | 0.000105 | 0.00012 | 0.000122 | 0.000129 | 0.000144 |
| 6 | 1.14E−06 | 1.21E−06 | 1.67E−06 | 1.98E−06 | 8.39E−06 | 9.79E−06 | 1.17E−05 | 1.71E−05 | 2.07E−05 | 2.07E−05 |
| 7 | 5.84E−07 | 1.14E−06 | 1.69E−06 | 3.64E−06 | 4.66E−06 | 5.04E−06 | 6.07E−06 | 6.19E−06 | 6.63E−06 | 6.65E−06 |
| 8 | 7.90E−06 | 9.40E−06 | 1.01E−05 | 2.08E−05 | 4.62E−05 | 4.66E−05 | 6.09E−05 | 8.06E−05 | 8.59E−05 | 8.65E−05 |
| 9 | 1.48E−06 | 2.27E−06 | 2.72E−06 | 6.05E−06 | 8.38E−06 | 9.93E−06 | 9.95E−06 | 1.04E−05 | 1.04E−05 | 1.35E−05 |
| 10 | 1.56E−06 | 7.20E−06 | 1.23E−05 | 1.36E−05 | 1.84E−05 | 1.89E−05 | 1.97E−05 | 2.32E−05 | 2.39E−05 | 2.46E−05 |
| 11 | 3.30E−07 | 2.43E−06 | 4.22E−06 | 4.73E−06 | 4.75E−06 | 5.80E−06 | 1.01E−05 | 1.07E−05 | 1.94E−05 | 2.21E−05 |
| 12 | 7.40E−07 | 8.86E−07 | 3.33E−06 | 4.21E−06 | 4.40E−06 | 1.30E−05 | 1.40E−05 | 1.72E−05 | 1.88E−05 | 2.14E−05 |
| 13 | 3.08E−06 | 6.22E−06 | 7.25E−06 | 8.10E−06 | 1.09E−05 | 1.09E−05 | 1.40E−05 | 1.52E−05 | 2.33E−05 | 3.75E−05 |
| 14 | 1.17E−06 | 4.29E−06 | 4.63E−06 | 8.72E−06 | 9.14E−06 | 1.14E−05 | 3.27E−05 | 4.40E−05 | 5.07E−05 | 7.77E−05 |
| 15 | 8.04E−06 | 1.87E−05 | 2.30E−05 | 2.49E−05 | 4.20E−05 | 4.42E−05 | 5.93E−05 | 8.93E−05 | 9.05E−05 | 9.50E−05 |
| 16 | 1.91E−07 | 5.36E−06 | 6.41E−06 | 1.06E−05 | 1.24E−05 | 1.33E−05 | 2.19E−05 | 2.31E−05 | 2.58E−05 | 2.94E−05 |
| 17 | 8.05E−07 | 1.01E−06 | 1.06E−06 | 1.33E−06 | 4.40E−06 | 5.13E−06 | 5.94E−06 | 6.12E−06 | 6.13E−06 | 9.04E−06 |
| 18 | 7.08E−07 | 1.28E−06 | 1.41E−06 | 2.28E−06 | 2.98E−06 | 3.45E−06 | 9.18E−06 | 1.19E−05 | 1.62E−05 | 1.80E−05 |
| 19 | 2.88E−06 | 3.00E−06 | 8.21E−06 | 1.25E−05 | 2.61E−05 | 2.76E−05 | 3.10E−05 | 3.11E−05 | 3.22E−05 | 3.57E−05 |
| 20 | 3.43E−05 | 4.14E−05 | 8.10E−05 | 8.30E−05 | 0.000112 | 0.000162 | 0.000166 | 0.000182 | 0.000183 | 0.000187 |
| 21 | 8.50E−07 | 1.46E−06 | 4.04E−06 | 2.04E−05 | 2.12E−05 | 2.60E−05 | 2.70E−05 | 2.82E−05 | 3.35E−05 | 3.94E−05 |
| 22 | 3.35E−05 | 5.03E−05 | 5.68E−05 | 7.48E−05 | 0.000126 | 0.000173 | 0.000217 | 0.000285 | 0.00032 | 0.000352 |
| 23 | 4.36E−06 | 1.68E−06 | 6.45E−06 | 7.66E−06 | 1.13E−05 | 1.21E−05 | 2.26E−05 | 2.77E−05 | 4.19E−05 | 4.55E−05 |
| 24 | 5.97E−06 | 1.92E−05 | 4.09E−05 | 4.20E−05 | 5.52E−05 | 6.28E−05 | 7.33E−05 | 7.68E−05 | 8.04E−05 | 9.32E−05 |
| 25 | 6.23E−07 | 6.45E−07 | 9.21E−07 | 1.29E−06 | 1.75E−06 | 1.87E−06 | 2.14E−06 | 2.19E−06 | 2.31E−06 | 3.05E−06 |
| 26 | 1.97E−07 | 5.34E−07 | 1.32E−06 | 1.42E−06 | 1.42E−06 | 1.65E−06 | 2.29E−06 | 5.10E−06 | 1.09E−05 | 1.45E−05 |
| 27 | 7.79E−06 | 9.77E−06 | 1.24E−05 | 1.47E−05 | 2.70E−05 | 3.11E−05 | 3.46E−05 | 3.76E−05 | 4.71E−05 | 5.98E−05 |
| 28 | 2.64E−06 | 3.89E−06 | 6.28E−06 | 9.92E−06 | 1.29E−05 | 1.65E−05 | 2.41E−05 | 2.60E−05 | 2.75E−05 | 2.99E−05 |
| 29 | 5.57E−07 | 1.94E−06 | 6.62E−06 | 1.04E−05 | 1.43E−05 | 1.50E−05 | 1.58E−05 | 1.65E−05 | 2.31E−05 | 2.41E−05 |
| 30 | 1.01E−06 | 1.29E−06 | 1.84E−06 | 3.00E−06 | 3.46E−06 | 4.25E−06 | 4.75E−06 | 4.94E−06 | 6.04E−06 | 6.39E−06 |
| 31 | 1.12E−06 | 2.66E−06 | 3.85E−06 | 4.98E−06 | 7.89E−06 | 8.24E−06 | 8.91E−06 | 1.65E−05 | 1.74E−05 | 1.90E−05 |
| 32 | 1.53E−06 | 2.55E−06 | 4.11E−06 | 9.54E−06 | 1.19E−05 | 1.21E−05 | 1.33E−05 | 1.55E−05 | 1.76E−05 | 1.80E−05 |
| 33 | 2.18E−06 | 7.21E−06 | 1.01E−05 | 1.92E−05 | 2.15E−05 | 2.16E−05 | 2.23E−05 | 3.04E−05 | 3.06E−05 | 3.20E−05 |
| 34 | 6.09E−07 | 7.37E−07 | 7.11E−06 | 7.92E−06 | 9.54E−06 | 1.30E−05 | 1.99E−05 | 2.48E−05 | 3.20E−05 | 3.32E−05 |
| 35 | 3.91E−07 | 6.84E−07 | 1.81E−06 | 5.50E−06 | 6.78E−06 | 9.66E−06 | 1.44E−05 | 1.62E−05 | 1.84E−05 | 2.52E−05 |
| 36 | 5.08E−08 | 2.75E−07 | 6.27E−07 | 1.49E−06 | 1.54E−06 | 1.95E−06 | 2.86E−06 | 8.61E−06 | 9.12E−06 | 1.40E−05 |

TABLE 2b-continued

| | Down Group | | | | | | | | | |
|---|---|---|---|---|---|---|---|---|---|---|
| | Ranking | | | | | | | | | |
| Selection | 1 | 2 | 3 | 4 | 5 | 6 | 7 | 8 | 9 | 10 |
| 37 | 5.47E−07 | 3.61E−06 | 3.75E−06 | 9.46E−06 | 2.12E−05 | 2.48E−05 | 3.82E−05 | 4.03E−05 | 5.10E−05 | 5.40E−05 |
| 38 | 3.20E−06 | 6.32E−06 | 1.76E−05 | 3.41E−05 | 4.82E−05 | 5.03E−05 | 7.82E−05 | 8.17E−05 | 0.000106 | 0.000112 |
| 39 | 3.53E−08 | 6.21E−08 | 2.28E−07 | 2.67E−07 | 3.58E−07 | 3.86E−07 | 4.88E−07 | 5.76E−07 | 6.54E−07 | 6.58E−07 |
| 40 | 1.01E−06 | 3.96E−06 | 4.62E−06 | 4.69E−06 | 6.05E−06 | 7.16E−06 | 1.02E−05 | 2.01E−05 | 2.04E−05 | 2.51E−05 |
| 41 | 3.27E−07 | 2.84E−06 | 3.99E−06 | 4.82E−06 | 7.09E−06 | 7.14E−06 | 8.98E−06 | 1.08E−05 | 1.09E−05 | 1.15E−05 |
| 42 | 4.94E−07 | 9.01E−07 | 9.28E−07 | 1.10E−06 | 1.28E−06 | 2.37E−06 | 2.56E−06 | 3.21E−06 | 3.23E−06 | 4.51E−06 |
| 43 | 5.99E−08 | 4.65E−07 | 6.93E−07 | 8.24E−07 | 8.94E−07 | 1.10E−06 | 1.90E−06 | 2.12E−06 | 2.33E−06 | 2.61E−06 |
| 44 | 5.44E−07 | 1.04E−06 | 1.64E−06 | 1.88E−06 | 2.16E−06 | 3.02E−06 | 4.54E−06 | 5.42E−06 | 5.69E−06 | 6.45E−06 |
| 45 | 3.21E−06 | 1.02E−05 | 1.43E−05 | 1.83E−05 | 3.73E−05 | 5.40E−05 | 5.71E−05 | 7.31E−05 | 8.19E−05 | 0.000108 |
| 46 | 6.75E−06 | 2.25E−05 | 2.78E−05 | 2.90E−05 | 4.49E−05 | 4.91E−05 | 6.49E−05 | 8.53E−05 | 8.72E−05 | 9.79E−05 |
| 47 | 3.39E−06 | 5.91E−06 | 6.99E−06 | 7.44E−06 | 9.34E−06 | 9.44E−06 | 1.01E−05 | 1.06E−05 | 1.24E−05 | 1.46E−05 |
| 48 | 1.61E−08 | 4.68E−08 | 5.21E−08 | 7.52E−07 | 1.11E−06 | 1.62E−06 | 4.48E−06 | 4.62E−06 | 5.03E−06 | 7.45E−06 |
| 49 | 1.30E−07 | 1.54E−07 | 2.00E−07 | 3.78E−07 | 6.78E−07 | 6.93E−07 | 9.87E−07 | 1.06E−06 | 1.57E−06 | 2.25E−06 |
| 50 | 1.61E−06 | 3.02E−06 | 3.49E−06 | 6.78E−06 | 7.16E−06 | 7.44E−06 | 1.48E−05 | 1.83E−05 | 1.91E−05 | 2.85E−05 |
| 51 | 1.71E−07 | 3.47E−07 | 9.70E−07 | 1.12E−06 | 1.27E−06 | 1.36E−06 | 2.85E−06 | 4.22E−06 | 4.52E−06 | 7.52E−06 |
| 52 | 1.62E−07 | 5.89E−06 | 9.77E−06 | 5.81E−06 | 6.16E−06 | 6.42E−06 | 9.11E−06 | 9.74E−06 | 1.10E−05 | 1.15E−05 |
| 53 | 6.54E−08 | 6.49E−07 | 7.92E−07 | 1.11E−06 | 2.38E−06 | 2.50E−06 | 2.83E−06 | 3.08E−06 | 3.45E−06 | 3.47E−06 |
| 54 | 5.79E−07 | 2.87E−06 | 3.55E−06 | 4.23E−06 | 4.46E−06 | 4.52E−06 | 5.27E−06 | 5.91E−06 | 6.57E−06 | 7.71E−06 |
| 55 | 5.52E−07 | 7.42E−07 | 1.02E−06 | 1.56E−06 | 1.57E−06 | 1.64E−06 | 1.68E−06 | 2.74E−06 | 3.36E−06 | 3.48E−06 |
| 56 | 1.79E−07 | 2.36E−07 | 2.71E−07 | 3.73E−07 | 4.89E−07 | 5.56E−07 | 1.26E−06 | 1.29E−06 | 1.36E−06 | 1.65E−06 |
| 57 | 8.63E−08 | 1.66E−07 | 4.96E−07 | 1.05E−06 | 1.26E−06 | 2.24E−06 | 2.29E−06 | 2.67E−06 | 3.14E−06 | 3.33E−06 |
| 58 | 4.58E−08 | 2.78E−07 | 5.89E−07 | 7.49E−07 | 1.41E−06 | 1.70E−06 | 2.11E−06 | 2.11E−06 | 2.14E−06 | 2.33E−06 |
| 59 | 1.42E−07 | 5.74E−07 | 6.33E−07 | 1.04E−06 | 1.28E−06 | 1.44E−06 | 3.21E−06 | 4.56E−06 | 4.77E−06 | 6.58E−06 |
| 60 | 9.17E−06 | 2.73E−05 | 4.89E−05 | 4.96E−05 | 5.90E−05 | 8.03E−05 | 0.000115 | 0.000128 | 0.000152 | 0.000166 |
| 61 | 6.41E−09 | 4.51E−08 | 1.60E−07 | 4.12E−07 | 7.04E−07 | 8.02E−07 | 9.24E−07 | 9.88E−07 | 1.12E−06 | 1.46E−06 |
| 62 | 6.31E−05 | 9.77E−05 | 0.000336 | 0.000385 | 0.000554 | 0.000687 | 0.000902 | 0.000944 | 0.00098 | 0.001056 |
| 63 | 2.15E−08 | 6.91E−08 | 7.46E−08 | 7.64E−08 | 9.61E−08 | 1.83E−07 | 3.63E−07 | 5.32E−07 | 6.82E−07 | 1.24E−06 |
| 64 | 9.71E−08 | 1.16E−07 | 1.33E−07 | 1.43E−07 | 2.99E−07 | 3.58E−07 | 4.31E−07 | 5.15E−07 | 5.56E−07 | 1.03E−06 |
| 65 | 4.45E−07 | 1.45E−06 | 4.17E−06 | 5.25E−06 | 5.84E−06 | 6.58E−06 | 6.88E−06 | 6.88E−06 | 7.00E−06 | 8.12E−06 |
| 66 | 1.99E−06 | 4.60E−06 | 6.41E−06 | 8.69E−06 | 9.70E−06 | 1.06E−05 | 1.25E−05 | 1.88E−05 | 2.70E−05 | 3.28E−05 |
| 67 | 9.11E−07 | 1.67E−06 | 4.35E−05 | 4.68E−05 | 4.70E−05 | 6.24E−05 | 8.11E−05 | 8.94E−05 | 8.97E−05 | 9.06E−05 |
| 68 | 9.27E−06 | 1.55E−05 | 1.59E−05 | 1.82E−05 | 1.92E−05 | 2.04E−05 | 2.37E−05 | 2.86E−05 | 2.92E−05 | 3.77E−05 |
| 69 | 9.89E−07 | 1.80E−06 | 1.97E−06 | 2.08E−06 | 2.48E−06 | 3.98E−06 | 4.44E−06 | 4.66E−06 | 4.99E−06 | 6.78E−06 |
| 70 | 1.60E−08 | 3.22E−08 | 4.94E−08 | 1.61E−07 | 2.32E−07 | 2.80E−07 | 3.21E−07 | 4.47E−07 | 1.04E−06 | 1.05E−06 |
| 71 | 1.79E−05 | 3.67E−05 | 9.18E−05 | 9.26E−05 | 0.000106 | 0.000109 | 0.000209 | 0.000244 | 0.000331 | 0.000373 |
| 72 | 1.25E−06 | 2.53E−06 | 2.70E−06 | 6.65E−06 | 1.69E−05 | 1.84E−05 | 3.78E−05 | 3.81E−05 | 3.95E−05 | 4.02E−05 |
| 73 | 3.80E−07 | 6.39E−07 | 1.71E−06 | 2.06E−06 | 2.26E−06 | 2.35E−06 | 2.46E−06 | 2.71E−06 | 3.23E−06 | 4.44E−06 |
| 74 | 9.65E−09 | 1.82E−06 | 5.89E−06 | 6.64E−06 | 7.30E−06 | 9.40E−06 | 1.04E−05 | 1.08E−05 | 1.38E−05 | 1.45E−05 |
| 75 | 3.39E−06 | 6.88E−06 | 8.96E−06 | 1.06E−05 | 3.34E−05 | 3.92E−05 | 5.60E−05 | 5.95E−05 | 6.28E−05 | 6.30E−05 |
| 76 | 7.05E−06 | 1.78E−05 | 1.79E−05 | 2.24E−05 | 2.44E−05 | 2.74E−05 | 3.06E−05 | 3.65E−05 | 4.68E−05 | 5.46E−05 |
| 77 | 1.11E−06 | 1.72E−06 | 2.62E−06 | 2.65E−06 | 2.66E−06 | 4.69E−06 | 5.05E−06 | 6.28E−06 | 7.60E−06 | 1.17E−05 |
| 78 | 1.02E−06 | 1.09E−06 | 2.33E−06 | 7.06E−06 | 1.43E−05 | 1.59E−05 | 1.82E−05 | 2.28E−05 | 3.24E−05 | 3.43E−05 |
| 79 | 2.37E−06 | 4.10E−06 | 4.50E−06 | 6.47E−06 | 6.66E−06 | 6.87E−06 | 7.09E−06 | 1.11E−05 | 2.43E−05 | 2.58E−05 |
| 80 | 3.70E−07 | 5.82E−07 | 2.88E−06 | 5.78E−06 | 7.30E−06 | 7.82E−06 | 1.11E−05 | 1.81E−05 | 2.20E−05 | 3.08E−05 |
| 81 | 9.72E−08 | 1.01E−07 | 2.79E−07 | 3.25E−07 | 3.49E−07 | 4.05E−07 | 4.92E−07 | 1.01E−06 | 1.29E−06 | 1.30E−06 |
| 82 | 6.01E−06 | 7.97E−06 | 8.10E−06 | 2.02E−05 | 2.04E−05 | 2.32E−05 | 2.96E−05 | 4.74E−05 | 5.53E−05 | 5.69E−05 |
| 83 | 1.35E−06 | 1.40E−06 | 2.01E−06 | 3.32E−06 | 9.37E−06 | 1.03E−05 | 1.79E−05 | 1.95E−05 | 2.85E−05 | 3.96E−05 |
| 84 | 6.99E−08 | 4.37E−07 | 1.11E−06 | 2.43E−06 | 3.47E−06 | 5.43E−06 | 7.49E−06 | 1.02E−05 | 1.56E−05 | 1.83E−05 |
| 85 | 6.54E−08 | 4.68E−06 | 4.95E−06 | 7.48E−06 | 9.55E−06 | 1.01E−05 | 1.82E−05 | 4.43E−05 | 8.21E−05 | 8.96E−05 |
| 86 | 5.05E−06 | 6.40E−06 | 7.22E−06 | 2.78E−05 | 3.26E−05 | 4.21E−05 | 5.31E−05 | 5.86E−05 | 6.65E−05 | 7.06E−05 |
| 87 | 2.22E−06 | 3.53E−06 | 3.57E−06 | 4.55E−06 | 5.88E−06 | 1.14E−05 | 1.74E−05 | 1.76E−05 | 1.81E−05 | 2.88E−05 |
| 88 | 1.90E−05 | 1.94E−05 | 1.94E−05 | 2.06E−05 | 2.14E−05 | 2.43E−05 | 2.65E−05 | 3.08E−05 | 3.50E−05 | 4.01E−05 |
| 89 | 3.66E−06 | 5.30E−06 | 6.93E−06 | 1.35E−05 | 1.39E−05 | 2.38E−05 | 4.32E−05 | 4.79E−05 | 5.15E−05 | 5.55E−05 |
| 90 | 6.21E−07 | 9.49E−07 | 1.00E−06 | 2.34E−06 | 7.04E−06 | 7.55E−06 | 1.27E−05 | 1.70E−05 | 1.94E−05 | 2.50E−05 |
| 91 | 6.97E−06 | 2.01E−05 | 2.73E−05 | 2.98E−05 | 3.20E−05 | 3.82E−05 | 5.20E−05 | 6.07E−05 | 7.16E−05 | 9.13E−05 |
| 92 | 6.92E−08 | 8.14E−08 | 1.19E−07 | 1.72E−07 | 2.53E−07 | 3.50E−07 | 3.86E−07 | 7.16E−07 | 7.87E−07 | 7.93E−07 |
| 93 | 1.98E−07 | 3.32E−07 | 3.46E−07 | 1.03E−06 | 1.17E−06 | 1.59E−06 | 1.87E−06 | 1.99E−06 | 2.26E−06 | 2.27E−06 |
| 94 | 2.95E−06 | 3.00E−06 | 1.14E−05 | 1.40E−05 | 4.08E−05 | 4.59E−05 | 4.82E−05 | 6.64E−05 | 7.12E−05 | 8.29E−05 |
| 95 | 1.60E−06 | 2.44E−06 | 4.05E−06 | 7.99E−06 | 8.20E−06 | 9.11E−06 | 9.22E−06 | 9.50E−06 | 9.82E−06 | 1.21E−05 |
| 96 | 1.22E−08 | 3.91E−08 | 9.08E−08 | 1.08E−07 | 2.00E−07 | 4.44E−07 | 4.52E−07 | 7.67E−07 | 8.20E−07 | 1.09E−06 |
| 97 | 4.39E−05 | 4.65E−05 | 5.56E−05 | 0.000105 | 0.000112 | 0.000182 | 0.000211 | 0.000212 | 0.000225 | 0.000247 |
| 98 | 8.87E−07 | 4.94E−06 | 5.11E−06 | 8.65E−06 | 2.48E−05 | 2.67E−05 | 3.39E−05 | 3.56E−05 | 4.30E−05 | 4.36E−05 |
| 99 | 3.40E−07 | 4.61E−07 | 4.92E−07 | 1.28E−06 | 2.65E−06 | 3.03E−06 | 3.55E−06 | 4.09E−06 | 4.35E−06 | 5.30E−06 |
| 100 | 1.48E−06 | 2.72E−06 | 3.86E−06 | 4.94E−06 | 1.64E−05 | 1.99E−05 | 2.03E−05 | 2.16E−05 | 2.30E−05 | 2.48E−05 |

TABLE 3

| Ranking | Gene | | | | | | | |
|---|---|---|---|---|---|---|---|---|
| | 22845 | 20252 | | 1236 | 785 | 4423 | 24143 | |
| | 26 | 11 | 1 | 11 | 18 | 19 | 15 | 1 |
| | 20 | 1 | 0.39284 | 4 | 17 | 4 | 24 | 0.54587 |
| | 9 | 0 | 0.21032 | 10 | 7 | 11 | 16 | 0.31047 |
| | 12 | 1 | 0.13493 | 5 | 8 | 3 | 9 | 0.19265 |
| | 4 | 3 | 0.082959 | 6 | 8 | 2 | 3 | 0.14035 |
| | 4 | 4 | 0.069754 | 4 | 6 | 8 | 7 | 0.11997 |
| | 4 | 4 | 0.05439 | 9 | 5 | 5 | 5 | 0.085956 |
| | 1 | 0 | 0.044642 | 5 | 6 | 5 | 3 | 0.070226 |
| | 1 | 0 | 0.036055 | 2 | 3 | 5 | 4 | 0.064407 |
| | 2 | 1 | 0.031745 | 3 | 4 | 1 | 2 | 0.05816 |
| | 83 | 25 | | 59 | 82 | 63 | 88 | |
| | 38.34144 | 12.30497 | | 20.00144 | 34.1139 | 27.57817 | 37.0775 | |
| | $a_i = 1$ | $a_i = 0.320931$ | | $a_i = 0.53945$ | $a_i = 0.92007$ | $a_i = 0.743798$ | $a_i = 1$ | |
| | 22845 | 20252 | | 1236 | 785 | 4423 | 24143 | | ratupdown 0.4282

The invention claimed is:

1. A method for determining whether an individual j suffering from an illness would respond to a predetermined treatment of the illness comprising:

selecting one or more genes from among a predetermined group of genes whose expression level is significantly different among a first group of individuals in a population in comparison with a second group of individuals within the population, wherein the first group of individuals is a group of individuals suffering from the illness that responded to the predetermined treatment to the illness and the second group of individuals is a group suffering from the illness that did not respond to the predetermined treatment, and wherein the selecting comprises for each of one or more selections of m individuals from the first group and n individuals from the second group determining a statistical significance of each gene i in an up group of the genes, the up group being a group of genes for which the expression level in the first group is greater than an expression level in the second group and the statistical significance of the gene i being calculated using an algebraic expression involving an average expression value of the gene i in the first group and a variance expression value of the gene i in the first group; and determining a statistical significance of each gene i in a down group of the genes, the down group being a group of genes for which the expression level in the first group is less than an expression level in the second group and the statistical significance of the gene i being calculated using an algebraic expression involving an average expression value of the gene i in the second group and a variance expression value of the gene i in the second group; and ranking the genes in the up group according to the number of times each gene received a highest statistical significance of the gene among the one or more selections of individuals;

ranking the genes in the down group according to the number of times each gene received a highest statistical significance of the gene among the one or more selections of individuals;

selecting a subset U' of genes in the up group having rankings above a first predetermined threshold; and selecting a subset of genes D' in the down group having highest rankings above a predetermined threshold;

obtaining a normalized statistical significance, $a_i$, for each gene i in U';

obtaining a normalized statistical significance, $a_i$, for each gene i in D';

calculating a score $d_j$, the score $d_j$ being obtained using an algebraic expression involving the gene expression levels of the individual j, $a_{ij}$, for genes i in U' and D';

determining that the individual j would respond to the treatment if the score has a predetermined relationship to a third predetermined threshold, the predetermined relationship being that the score dj is below the third predetermined threshold or that the score is above the predetermined threshold; and determining that the individual j would not respond to the treatment if the score $d_j$ does not have the predetermined relationship to the third predetermined threshold, wherein one or more step is performed on a suitably programmed computer.

2. The method according to claim 1, wherein the illness is breast cancer or hepatitis.

3. The method according to claim 1, wherein the illness is breast cancer.

4. The method according to claim 1, wherein the illness is hepatitis.

5. The method according to claim 1, wherein the score $d_j$ is calculated as $$dj = \sum_{i \in U'} a_i a_{ij} - \sum_{i \in D'} a_i a_{ij}.$$

6. The method according to claim 5, further comprising comparing the score $d_j$ to a cut off value, the individual j being determined to be in a success group if the score $d_j$ is above the cut off, and the individual j being determined to be in a failure group if the score $d_j$ is below the cut off.

7. The method according to claim 6, wherein the cut off is given by $$\frac{(\mu^s + \sigma^s) + (\mu^f - \sigma^f)}{2},$$

where
- $\mu^s$ and $\sigma^s$ are average and standard deviation values of expression level, respectively, of the gene in the success group, and
- $\mu^f$ and $\sigma^f$ are average and standard deviation values of expression level, respectively, of the gene in the failure group.

8. The method according to claim 5, further comprising:

calculating the median of the scores $d_j$ in the success group, $m_s$, and the median of the scores in the failure group, $m_f$, of the learning group;

calculating the score $d_j$ of the individual to be tested;

determining to which of the two medians the tested individual's score is closest, the individual being determined to belong to the success group if the score is closest to the median of the success group, and the individual being determined to belong to the failure group if the score is closest to the median of the failure group.

* * * * *

UNITED STATES PATENT AND TRADEMARK OFFICE
CERTIFICATE OF CORRECTION

PATENT NO. : 8,423,296 B2  
APPLICATION NO. : 12/083153  
DATED : April 16, 2013  
INVENTOR(S) : Yoav Smith Page 1 of 1

It is certified that error appears in the above-identified patent and that said Letters Patent is hereby corrected as shown below:

In the Claims;

Column 20, Claim 1, Line 31

Please delete "treatment if the score has a predetermined"

and replace with -- treatment if the score $d_j$ has a predetermined --

Signed and Sealed this
Twenty-seventh Day of August, 2013

Teresa Stanek Rea
*Acting Director of the United States Patent and Trademark Office*